US008235955B2

(12) United States Patent
Blott et al.

(10) Patent No.: US 8,235,955 B2
(45) Date of Patent: Aug. 7, 2012

(54) WOUND TREATMENT APPARATUS AND METHOD

(75) Inventors: Patrick L. Blott, Barmby Moor (GB); Edward Y. Hartwell, Hull (GB); Julian Lee-Webb, Copmanthorpe (GB); Derek Nicolini, Borough (GB)

(73) Assignee: Smith & Nephew PLC, London (GB)

( * ) Notice: Subject to any disclaimer, the term of this patent is extended or adjusted under 35 U.S.C. 154(b) by 810 days.

(21) Appl. No.: 11/919,355

(22) PCT Filed: Apr. 27, 2006

(86) PCT No.: PCT/GB2006/001551
§ 371 (c)(1),
(2), (4) Date: Nov. 17, 2008

(87) PCT Pub. No.: WO2006/114637
PCT Pub. Date: Nov. 2, 2006

(65) Prior Publication Data
US 2009/0306609 A1    Dec. 10, 2009

(30) Foreign Application Priority Data
Apr. 27, 2005    (GB) .................................. 0508528.7

(51) Int. Cl.
*A61F 13/00* (2006.01)
(52) U.S. Cl. .................. 604/305; 604/317; 604/543
(58) Field of Classification Search .................. 604/315, 604/19, 289–290, 304–308, 317, 319–323, 604/327, 540, 543
See application file for complete search history.

(56) References Cited

U.S. PATENT DOCUMENTS

| | | | |
|---|---|---|---|
| 2,280,915 | A | 4/1941 | Johnson |
| 3,171,410 | A | 3/1965 | Towle et al. |
| 3,624,821 | A | 11/1971 | Henderson |
| 3,633,567 | A | 1/1972 | Sarnoff |
| 3,874,387 | A | 4/1975 | Barbieri |
| 3,993,080 | A | 11/1976 | Loseff |
| 4,112,947 | A | 9/1978 | Nehring |
| 4,136,696 | A | 1/1979 | Nehring |

(Continued)

FOREIGN PATENT DOCUMENTS
DE    3935818 A1    5/1991
(Continued)

OTHER PUBLICATIONS
U.S. Appl. No. 12/300,636, filed Nov. 12, 2008, Fry et al.
(Continued)

*Primary Examiner* — Tatyana Zalukaeva
*Assistant Examiner* — Benedict L Hanrahan
(74) *Attorney, Agent, or Firm* — Knobbe, Martens, Olson & Bear LLP

(57) ABSTRACT

An apparatus for cleansing wounds in which irrigant fluid from a reservoir connected to a conformable wound dressing and wound exudate from the dressing are moved by a device (which may be a single pump or two pumps) for moving fluid through a flow path which passes through the dressing and a means for providing simultaneous aspiration and irrigation of the wound, and means for stressing the wound bed and optionally tissue surrounding the wound. The former removes materials deleterious to wound healing, while distributing materials that are beneficial in promoting wound healing over the wound bed. The latter promotes wound healing. The dressing and a method of treatment using the apparatus.

49 Claims, 13 Drawing Sheets

U.S. PATENT DOCUMENTS

Figure 1:
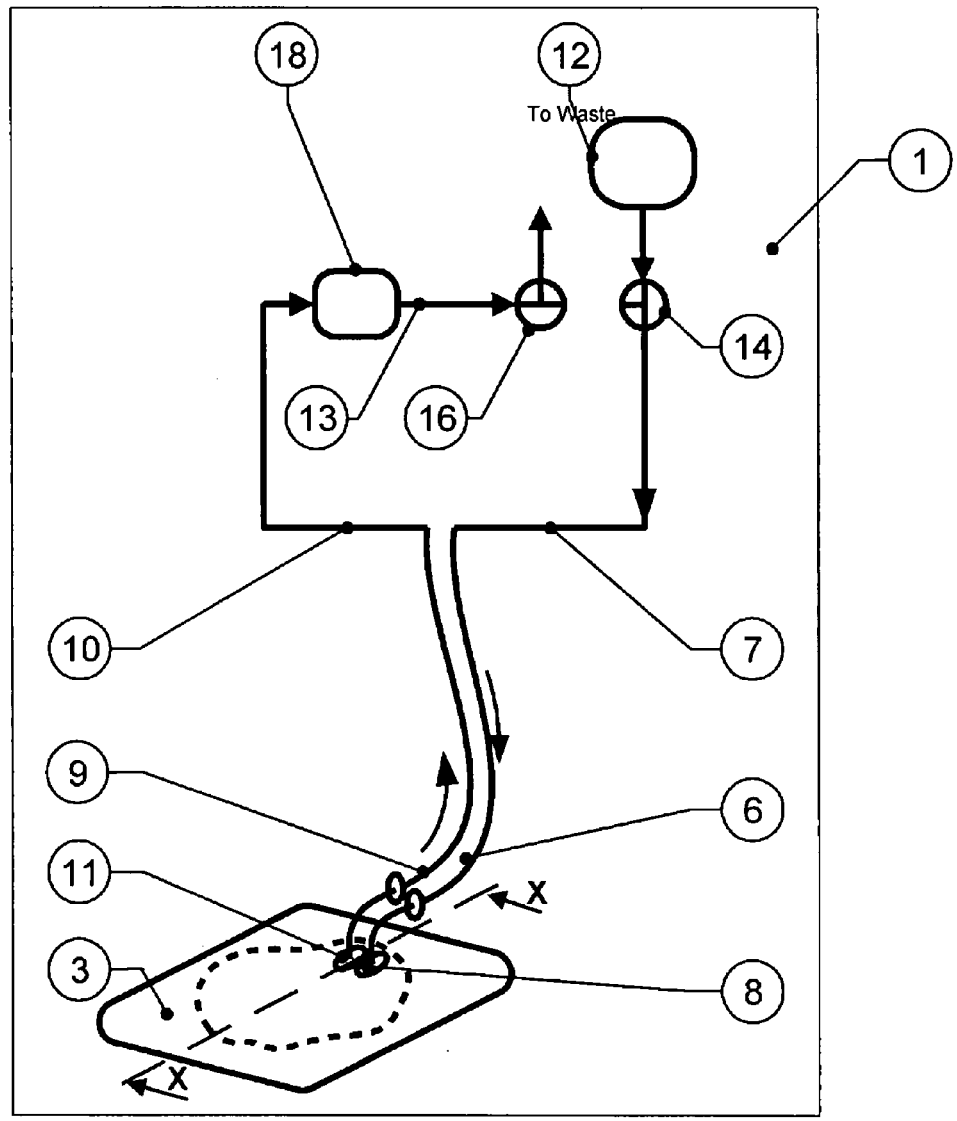
Figure 1:
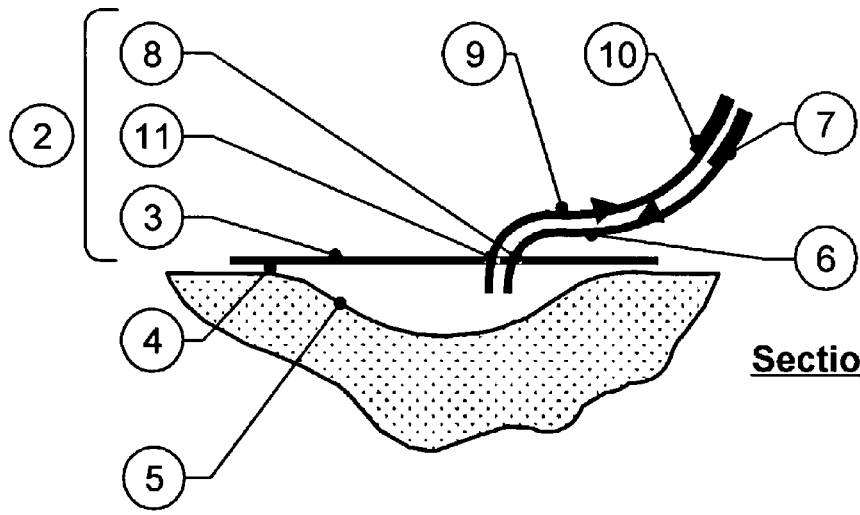

| | | | |
|---|---|---|---|
| 4,178,938 A | 12/1979 | Au | |
| 4,180,074 A | 12/1979 | Murry et al. | |
| 4,224,945 A | 9/1980 | Cohen | |
| 4,316,466 A | 2/1982 | Babb | |
| 4,382,441 A | 5/1983 | Svedman | |
| 4,529,402 A | 7/1985 | Weilbacher et al. | |
| 4,573,965 A | 3/1986 | Russo | |
| 4,778,446 A | 10/1988 | Jensen | |
| 4,792,328 A | 12/1988 | Beck et al. | |
| 4,921,488 A | 5/1990 | Maitz et al. | |
| 4,936,834 A | 6/1990 | Beck et al. | |
| 4,969,880 A | 11/1990 | Zamierowski | |
| 5,073,172 A | 12/1991 | Fell | |
| 5,100,396 A | 3/1992 | Zamierowski | |
| 5,176,663 A | 1/1993 | Svedman et al. | |
| 5,261,893 A | 11/1993 | Zamierowski | |
| 5,328,614 A | 7/1994 | Matsumura | |
| 5,358,494 A | 10/1994 | Svedman | |
| 5,360,398 A | 11/1994 | Grieshaber et al. | |
| 5,380,280 A | 1/1995 | Peterson | |
| 5,498,338 A | 3/1996 | Kruger et al. | |
| 5,549,584 A | 8/1996 | Gross | |
| 5,636,643 A | 6/1997 | Argenta et al. | |
| 5,645,081 A | 7/1997 | Argenta et al. | |
| 5,676,650 A | 10/1997 | Grieshaber et al. | |
| 5,678,564 A | 10/1997 | Lawrence et al. | |
| 5,759,570 A | 6/1998 | Arnold | |
| 5,830,176 A | 11/1998 | Mackool | |
| 5,911,222 A | 6/1999 | Lawrence et al. | |
| 6,159,160 A | 12/2000 | Hsei et al. | |
| 6,254,567 B1 | 7/2001 | Treu et al. | |
| 6,398,767 B1 | 6/2002 | Fleischmann | |
| 6,458,109 B1 | 10/2002 | Henley et al. | |
| 6,465,708 B1 | 10/2002 | Augustine | |
| 6,626,827 B1 | 9/2003 | Felix et al. | |
| 6,685,681 B2 | 2/2004 | Lockwood et al. | |
| 6,695,824 B2 | 2/2004 | Howard et al. | |
| 6,752,794 B2 | 6/2004 | Lockwood et al. | |
| 6,755,807 B2 | 6/2004 | Risk et al. | |
| 6,979,324 B2 | 12/2005 | Bybordi et al. | |
| 7,004,915 B2 | 2/2006 | Boynton et al. | |
| 7,077,832 B2 | 7/2006 | Fleischmann | |
| 7,108,683 B2 | 9/2006 | Zamierowski | |
| 7,195,624 B2 | 3/2007 | Lockwood | |
| 7,214,202 B1 | 5/2007 | Vogel et al. | |
| 7,216,651 B2 | 5/2007 | Argenta et al. | |
| 7,503,910 B2 | 3/2009 | Adahan | |
| 7,524,315 B2 * | 4/2009 | Blott et al. | 604/543 |
| 7,534,927 B2 | 5/2009 | Lockwood | |
| 7,611,500 B1 | 11/2009 | Lina et al. | |
| 7,625,362 B2 | 12/2009 | Boehringer et al. | |
| 7,759,538 B2 | 7/2010 | Fleischmann | |
| 7,811,269 B2 | 10/2010 | Boynton et al. | |
| 7,828,782 B2 | 11/2010 | Suzuki | |
| 2001/0029956 A1 | 10/2001 | Argenta | |
| 2001/0034499 A1 | 10/2001 | Sessions et al. | |
| 2002/0161346 A1 | 10/2002 | Lockwood et al. | |
| 2003/0021775 A1 | 1/2003 | Freeman | |
| 2003/0040687 A1 | 2/2003 | Boynton et al. | |
| 2003/0050594 A1 | 3/2003 | Zamierowski | |
| 2003/0108587 A1 | 6/2003 | Orgill et al. | |
| 2003/0144619 A1 | 7/2003 | Augustine | |
| 2003/0171675 A1 | 9/2003 | Rosenberg | |
| 2004/0054338 A1 | 3/2004 | Bybordi et al. | |
| 2006/0155260 A1 | 7/2006 | Blott et al. | |
| 2007/0021697 A1 | 1/2007 | Ginther et al. | |
| 2007/0021698 A1 | 1/2007 | Fleischmann | |
| 2007/0038172 A1 | 2/2007 | Zamierowski | |
| 2007/0066945 A1 | 3/2007 | Martin | |
| 2007/0129660 A1 | 6/2007 | McLeod et al. | |
| 2007/0129707 A1 | 6/2007 | Blott et al. | |
| 2007/0141128 A1 | 6/2007 | Blott et al. | |
| 2007/0167926 A1 | 7/2007 | Blott et al. | |
| 2007/0219471 A1 | 9/2007 | Johnson et al. | |
| 2007/0219497 A1 | 9/2007 | Johnson et al. | |
| 2007/0293830 A1 | 12/2007 | Martin | |
| 2008/0125698 A1 | 5/2008 | Gerg et al. | |
| 2009/0012483 A1 * | 1/2009 | Blott et al. | 604/315 |
| 2009/0036873 A1 | 2/2009 | Nielsen et al. | |
| 2009/0312723 A1 * | 12/2009 | Blott et al. | 604/290 |
| 2011/0213319 A1 | 9/2011 | Blott et al. | |
| 2011/0213320 A1 | 9/2011 | Blott et al. | |

FOREIGN PATENT DOCUMENTS

| | | |
|---|---|---|
| DE | 40 12 232 A1 | 10/1991 |
| DE | 41 02 684 A1 | 8/1992 |
| DE | 198 44 355 | 4/2000 |
| EP | 0020662 B1 | 7/1984 |
| EP | 0880953 B1 | 5/1998 |
| EP | 0 777 504 | 10/1998 |
| EP | 1 897 569 | 8/2002 |
| FR | 1 163 907 | 10/1958 |
| GB | 114754 | 4/1918 |
| GB | 641061 | 8/1950 |
| GB | 1 224 009 A | 3/1971 |
| GB | 1549756 A | 8/1979 |
| GB | 2378392 A | 2/2003 |
| JP | 2001314479 A | 11/2001 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 00/07653 | 2/2000 |
| WO | WO 00/50143 A | 8/2000 |
| WO | WO 01/37773 | 5/2001 |
| WO | WO 02/083046 A1 | 10/2002 |
| WO | WO 02/092783 | 11/2002 |
| WO | WO 03/101508 | 12/2003 |
| WO | WO 2004/024300 | 3/2004 |
| WO | WO 2004/037334 A | 5/2004 |
| WO | WO 2005/046761 | 5/2005 |
| WO | WO 2005/046762 | 5/2005 |
| WO | WO 2005/051461 A | 6/2005 |
| WO | WO 2005/070480 | 8/2005 |
| WO | WO 2005/082435 A | 9/2005 |
| WO | WO 2005/082435 A1 | 9/2005 |
| WO | WO 2005/105174 A | 11/2005 |
| WO | WO 2005/105175 | 11/2005 |
| WO | WO 2005/105176 | 11/2005 |
| WO | WO 2006/052745 | 5/2006 |
| WO | WO 2007/087809 | 8/2007 |
| WO | WO 2008/010094 | 1/2008 |
| WO | WO 2008/030872 | 3/2008 |
| WO | WO 2008/036360 | 3/2008 |
| WO | WO 2008/048481 | 4/2008 |

OTHER PUBLICATIONS

International Search Report for International Application No. PCT/GB2006/001551, date of mailing Jan. 19, 2007, in 4 pages.
U.S. Appl. No. 10/599,722, filed Oct. 6, 2006, Blott et al.
U.S. Appl. No. 10/599,725, filed Oct. 6, 2006, Blott et al.
U.S. Appl. No. 10/599,728, filed Oct. 6, 2006, Blott et al.
U.S. Appl. No. 11/919,354, filed Oct. 26, 2007, Blott et al.
U.S. Appl. No. 11/919,369, filed Oct. 26, 2007, Blott et al.
U.S. Appl. No. 11/957,860, filed Dec. 17, 2007, Blott et al.
U.S. Appl. No. 12/066,578, filed Mar. 12, 2008, Blott et al.
U.S. Appl. No. 12/066,585, filed Mar. 12, 2008, Blott et al.
U.S. Appl. No. 12/066,730, filed Mar. 13, 2008, Blott et al.
U.S. Appl. No. 12/094,963, filed May 23, 2008, Dagger.
Aubrey, D.A., et al., Treatment of the Perineal Wound after Proctectomy by Intermittent Irrigation, Arch. Surg., Oct. 1984, vol. 119, pp. 1141-1144.
Chariker, M.E., et al, Effective Management of Incisional and Cutaneous Fistulae with Closed Suction Wound Drainage, Contemporary Surgery, Jun. 1989, vol. 34 USA, pp. 59-63.
Dilmaghani et al., A Method for Closed Irrigation and Suction Therapy in Deep Wound Infections, Journal of Bone and Joint Surgery, 1969, vol. 51-A, No. 2, pp. 323-342.
Hartz, R.S., et al., Healing of the Perineal Wound, Arch. Surg., Apr. 1980, vol. 115, pp. 471-474.
International Search Report for International Application No. PCT/GB2006/001551, Date of Mailing Jan. 19,2007 in 4 pages.

International Preliminary Report for International Application No. PCT/GB/2006/001551, Date of Report Issuance Oct. 30,2007 in 8 pages.

NURSING75, Wound Suction: Better Drainage with Fewer Problems, Nursing, vol. 5, No. 10, Oct. 1975, pp. 52-55.

Svedman, P., Irrigation Treatment in Split-Thickness Skin Grafting of Intractable Leg Ulcers, Scand J. Plast. Reconst. Surg., 1985, vol. 19, pp. 211-213.

Svedman, P., Irrigation Treatment of Leg Ulcers, The Lancet, Sep. 1983, pp. 532-534.

Svedman, P., A Dressing Allowing Continuous Treatment of a Biosurface, IRCS Med. Science: Biomed. Tech.; Clinic. Med.; Surg. and Transplantation, 1979, vol. 7, p. 221.

Svedman, P., et al., A Dressing System Providing Fluid Supply and Suction Drainage Used for Continuous or Intermittent irrigation, Annals of Plastic Surgery, vol. 17, No. 2, Aug. 1986, pp. 125-133.

Swift, et al, Quorum Sensing in *Aeromonas hydrophila* and *Aeromonas salmoncida*: Identification of LuxRI Homologs AhyRI and AsaRI and Their Cognate N-Acylhomoserine Lactone Signal Molecules, J. Bacteriol., 1997, vol. 179, No. 17, pp. 5271-5281.

Teder and Svedman et al., Continuous Wound Irrigation in the Pig, Journal of Investigative Surgery, 1990, vol. 3, pp. 399-407.

Tribble, David E. M.D., An Improved Sump Drain-Irrigation Device of Simple Construction, Archives of Surgery New York, 1972, vol. 105, pp. 511-513.

Urschel, J.D., et al., The Effect of Mechanical Stress on Soft and Hard Tissue Repair; A Review, Br. Journ. Plast. Surg., 1988, vol. 41, pp. 182-186.

Vijanto, J. and J. Raekallio, Local Hyperalimentation of Open Wounds, Br. J. surg., 1976, vol. 63, pp. 427-430.

Westaby, S., et al., A Wound Irrigation Device, The Lancet, Sep. 2, 1978, pp. 503-504.

Wooding-Scott, Margaret, et al., No Wound is Too Big for Resourceful Nurses, RN, USA, Dec. 1988, pp. 22-25.

U.S. Appl. No. 12/416,829, filed Apr. 1, 2009, published as 2009/0254054 and its ongoing prosecution history including without limitation Office Actions, Amendments, Remarks, and any other potentially relevant documents, Oct. 8, 2009, Blott et al.

U.S. Appl. No. 12/762,250, filed Apr. 16, 2010, published as 2010/0274167, and its ongoing prosecution history including without limitation Office Actions, Amendments, Remarks, and any other potentially relevant documents, Oct. 28, 2010, Martin et al.

U.S. Appl. No. 12/832,002, filed Jul. 7, 2010, published as 2011/0004171, and its ongoing prosecution history including without limitation Office Actions, Amendments, Remarks, and any other potentially relevant documents, Jan. 6, 2011, Blott et al.

U.S. Appl. No. 12/832,032, filed Jul. 7, 2010, published as 2011/0009835, and its ongoing prosecution history including without limitation Office Actions, Amendments, Remarks, and any other potentially relevant documents, Jan. 13, 2011, Blott et al.

U.S. Appl. No. 10/599,722, filed Sep. 19, 2008, published as 2009/0012483, and its ongoing prosecution history including without limitation Office Actions, Amendments, Remarks, and any other potentially relevant documents, Jan. 8, 2009, Blott et al.

U.S. Appl. No. 12/976,949, filed Dec. 22, 2010, and its ongoing prosecution history including without limitation Office Actions, Amendments, Remarks, and any other potentially relevant documents.

U.S. Appl. No. 12/976,935, filed Dec. 22, 2010, and its ongoing prosecution history including without limitation Office Actions, Amendments, Remarks, and any other potentially relevant documents.

U.S. Appl. No. 10/599,725, filed Sep. 22, 2008, published as 2009-0069759, and its ongoing prosecution history including without limitation Office Actions, Amendments, Remarks, and any other potentially relevant documents, Mar. 12, 2009, Blott et al.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajecar, 1986, No. 3-4, pp. 161-164 (with English translation).

Written Opinion of application No. PCT/ GB2006/001551; mailing date Oct. 27, 2007 in 7 pages.

* cited by examiner

Section View on X-X

Section Through X-X

Section Through X-X

WOUND TREATMENT APPARATUS AND METHOD

This application is the U.S. national phase of International Application No. PCT/GB2006/001551 filed on Apr. 27, 2006 and published in English on Nov. 2, 2006 as International Publication No. WO 2006/114637 A2, which application claims priority to Great Britain Patent Application No. 0508528.7 filed on Apr. 27, 2005, the contents of the foregoing are incorporated herein by reference.

The present invention relates to apparatus and a medical wound dressing for aspirating, irrigating and/or cleansing wounds, and a method of treating wounds using such apparatus for aspirating, irrigating and/or cleansing wounds.

It relates in particular to such an apparatus, wound dressing and method that can be easily applied to a wide variety of, but in particular chronic, wounds, to cleanse them of materials that are deleterious to wound healing, whilst distributing materials that are beneficial in some therapeutic aspect, in particular to wound healing.

Aspirating and/or irrigating apparatus are known, and tend to be used to remove wound exudate during wound therapy. In known forms of such wound therapy, aspiration and irrigation of the wound generally take place sequentially.

Each Part of the Therapy Cycle is Beneficial in Promoting Wound Healing:

Aspiration applies a negative pressure to the wound, which is beneficial in itself in promoting wound healing by removing materials deleterious to wound healing with the wound exudate, reducing bacterial load, combating peri-wound oedema, increasing local blood flow to the wound and encouraging the formation of wound bed granulation tissue.

Irrigation cleanses wounds of materials that are deleterious to wound healing by diluting and moving wound exudate (which is typically relatively little fluid and may be of relatively high viscosity and particulate-filled.

Additionally, relatively little of beneficial materials involved in promoting wound healing (such as cytokines, enzymes, growth factors, cell matrix components, biological signalling molecules and other physiologically active components of the exudate) are present in a wound, and are not well distributed in the wound, i.e. they are not necessarily present in parts of the wound bed where they can be potentially of most benefit. These may be distributed by irrigation of the wound and thus aid in promoting wound healing.

The irrigant may additionally contain materials that are potentially or actually beneficial in respect of wound healing, such as nutrients for wound cells to aid proliferation, and gases, such as oxygen. These may be distributed by irrigation of the wound and thus aid in promoting wound healing.

If aspiration and irrigation therapy is applied sequentially to a wound, the two therapies, each of which is beneficial in promoting wound healing, can only be applied intermittently.

Thus, the wound will lose the abovementioned known beneficial effects of aspiration therapy on wound healing, at least in part, while that aspiration is suspended during irrigation.

Additionally, for a given aspirate flow, whilst materials that are potentially or actually deleterious in respect of wound healing are removed from wound exudate, the removal in a given time period of application of the total irrigate and/or aspirate therapy will normally be less effective and/or slower than with continuous application of aspiration.

Even less to be desired, is that while aspiration is not applied to the wound, wound exudate and materials deleterious to wound healing (such as bacteria and debris, and iron II and iron III and for chronic wounds proteases, such as serine proteases) will pool on the wound bed and hinder wound healing, especially in a highly exuding wound. The influx of local oedema will also add to the chronicity of the wound. This is especially the case in chronic wounds.

Depending on the relative volumes of irrigant and wound exudate, the mixed exudate-irrigant fluid and may be of relatively high viscosity and/or particulate-filled. Once it is present and has pooled, it may be more difficult to shift by the application of aspiration in a conventional sequential aspirate—irrigate—dwell cycle than with continuous simultaneous aspiration and irrigation of the wound, owing to the viscosity and blockage in the system.

The wound will also lose the abovementioned beneficial effects of irrigation therapy on wound healing, at least in part, while that irrigation is suspended during aspiration.

These benefits in promoting wound healing include the movement of materials that are beneficial in promoting wound healing, such as those mentioned above.

Additionally, for a given irrigant flow, the cleansing of the wound and the distribution by irrigation of the wound of such beneficial materials in a given time period of application of the total irrigate and/or aspirate therapy when such therapy is in a conventional sequential aspirate—irrigate—dwell cycle will normally be less effective and/or slower than with continuous application of aspiration.

Such known forms of aspiration and/or irrigation therapy systems also often create a wound environment that may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

The relevant devices tend not to be portable.

It thus would be desirable to provide a system of aspiration and irrigation therapy for a wound, which
can remove wound exudate and materials deleterious to wound healing from contact with the wound bed,
whilst simultaneously cleansing it and distributing materials that are beneficial in promoting wound healing across it.

It is further desirable to provide a system which:
a) obviates at least some of the abovementioned disadvantages of known aspiration and/or irrigation systems, and
b) is portable.

Vascular supply to, and aspiration in, tissue underlying and surrounding the wound is often compromised.

It is further desirable to provide a system of therapy that also promotes vascular supply to tissue underlying and surrounding a wound, promoting wound healing.

Additionally, known forms of wound dressing and aspiration and/or irrigation therapy systems often create a wound environment under the backing layer that may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

It is an object of the present invention to provide a system of therapy which can:
i) remove materials deleterious to wound healing from wound exudate.
ii) creates stress or strain across the wound bed and optionally tissue surrounding the wound, e.g. by applying an optionally varying positive and/or negative pressure to the wound.

The terms stress and strain have slightly different meanings, but in the context of this application, are often used interchangeably. "Stress" refers to a physical force acting upon a surface or structure, in this case a wound bed. Stress is typically defined as force per unit area on a surface. "Strain" refers to a mechanical deflection of a surface or structure caused by stress, again in this case a wound bed. Stress may cause strain, or vice versa, but in the context of the present application, where the term stress is used, it should be understood to refer to stress or strain of the wound bed. For example, applying a positive pressure to a wound bed will apply a stress to the surface of the wound bed, but will also apply a strain as the wound bed is a resilient structure which will deflect as a result of the pressure. On the other hand deflection of the wound bed in one area (i.e. applying a strain) may cause stress and/or strain in another area. Accordingly where the term stress or strain is used in the present application, they should not be taken in their strict mechanical meaning (although that may be appropriate) but should be understood to mean the deflection or application of force to the cells of the wound bed and or surrounding areas.

Such a stress or strain across the wound bed and optionally tissue surrounding the wound, e.g. an optionally varying positive and/or negative pressure applied to the wound, has been found to result in an increase in improvements to wound healing, such as an increase in cell proliferation, revascularisation, improved breaking strength and reduction of wound recurrence.

The resultant tissue growth has a strong three-dimensional structure adhering well to and growing from the wound bed. It also stimulates blood flow in underlying tissue and optionally tissue surrounding the wound.

Removal of fluid by optionally varying negative pressure leads to reduction of interstitial oedema and pressure directly affecting the lymphatic and capillary system, restoring lymph function.

All of these are beneficial to wound healing.

The application of stress and/or strain to a wound bed to improve healing is equally applicable to both sequential systems (i.e. empty/fill cycles) or simultaneous irrigate/aspirate systems. Although it is generally preferred to use a simultaneous system due to the benefits of such a system, there may be circumstances where a sequential system is preferred, e.g. due to cost.

According to a first aspect of the present invention there is provided an apparatus for aspirating, irrigating and/or cleansing of a wound, comprising
a) a fluid flow path, comprising a conformable wound dressing, having a backing layer which is capable of forming a relatively fluid-tight seal or closure over a wound and at least one pipe which passes through and/or under the wound-facing face to allow irrigation and/or aspiration of a wound, and wherein the point at which the at least one pipe passes through and/or under the wound-facing face forms a relatively fluid-tight seal or closure over the wound, when in use;
b) a fluid reservoir connectable by a fluid supply tube to the at least one pipe and
c) at least one device for moving fluid through the wound dressing to the wound and/or moving fluid from the wound; characterised in that the apparatus it comprises
d) means for applying stress to the wound bed and optionally tissue surrounding the wound.

Generally it is preferred that the apparatus has at least one inlet pipe for connection to a fluid supply tube to allow irrigation and
at least one outlet pipe for connection to a fluid offtake tube to allow aspiration
each of which passes through and/or under the wound-facing face.

Such an embodiment is suitable for both sequential and simultaneous systems, whereas a single pipe system is only suitable for sequential fill/empty cycles.

In one embodiment the present invention provides means for providing simultaneous aspiration and irrigation of the wound,
such that fluid may be supplied to fill the flowpath from the fluid reservoir via the fluid supply tube (optionally via means for supply flow regulation) while fluid is aspirated by a device through the fluid offtake tube (optionally or as necessary via means for aspirate flow regulation).

Such an embodiment is particularly suitable for simultaneous irrigation and aspiration and thus forms a preferred embodiment of the present invention.

Where any pipe is described in connection with the apparatus as being connected or for connection to a (mating end of a) tube, e.g. a fluid supply tube or fluid offtake tube, the pipe and the tube may form a single integer in the flow path.

As noted hereinbefore, the present invention in this aspect advantageously provides a means for combining more than one therapy in a single dressing system, such as
a) removal of materials deleterious to wound healing from wound exudate, and
b) promoting wound healing, by stimulating new tissue growth adhering well to and growing from the wound bed, by creating stress across the wound bed and optionally tissue surrounding the wound.

In all relevant embodiments of the present apparatus for irrigating, stressing and/or cleansing wounds, it is advantageous that it additionally, where appropriate, comprises a system which can regulate the pressure on the wound bed, under the wound dressing.

Preferably such a system is a conventional automated, programmable system which can maintain the wound at or near an appropriate, desired stress to the wound bed and optionally tissue surrounding the wound, to an appropriate, desired programme while moving fluid over the wound bed at an appropriate, desired rate.

Examples of suitable means for the stimulation of the healing of wounds and tissue adhering well to and growing from the wound bed include applying mechanical stimulus to the wound bed and optionally tissue surrounding the wound via the wound dressing and/or via the fluid under dressing.

Examples of suitable ways in which this can in turn be achieved include applying an optionally varying positive and/or negative pressure at any appropriate point for stressing the wound.

The amplitude of the positive and/or negative pressure on the wound bed and optionally tissue surrounding the wound and/or the fluid thereover may be constant, but more usually is varied, preferably cyclically, either randomly or regularly. Such cyclical variation of the pressure applied to the wound is effectively the application of an amplitude waveform at a desired frequency to apply a desired level of stress to the wound bed and optionally tissue surrounding the wound (it should be noted that application of a varying pressure may cause strain to the surface of the wound, i.e. deflection of the wound bed, but this is envisaged in the term stress as used herein).

The desired level and regime of stress to the wound bed and optionally tissue surrounding the wound may be applied conventionally by varying the positive and/or negative pressure applied to the wound bed, e.g. by
a) varying the rate of the means for moving fluid over the wound bed as appropriate or desired, e.g. the rate of any pump used to apply positive or negative pressure to the wound bed at any appropriate point for stressing the wound, b) bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or programme, and/or c) varying the pressure in any inflatable filler within the wound dressing as appropriate or desired, as described in more detail hereinafter.

Preferably, such regular or random variation of the positive and/or negative pressure applied to the wound will be effected by conventional process control devices and/or software.

The stimulation of the healing of wounds in the present invention may also be effected by agitation of the wound bed and/or creating intermittent flow and/or turbulence to stimulate the cells. This can be done preferably by regularly or randomly pulsing a positive and/or negative pressure applied to the wound at any appropriate point for this purpose.

Such pulsed variation of the pressure applied to the wound is again effectively the application of an amplitude waveform at a desired frequency to apply a desired level of stress to the wound bed and optionally tissue surrounding the wound.

Pulsing the pressure on the wound may advantageously also provide a means to over-ride pain, similar to TENS.

The range of variation of the pulsed positive and/or negative pressure applied to the wound will be substantially less than the maximum levels of pressure referred to below, i.e. less than 50% atm and typically significantly lower.

The frequencies of such pulsed stressing across the wound will be substantially higher than those of the cycles of positive and/or negative pressure to the wound bed and optionally tissue surrounding the wound for the stimulation of the healing of wounds referred to above.

The range of variation of the pulsed positive and/or negative pressure applied to the wound will generally be substantially less than the maximum levels of pressure and than the range of variation in the levels of pressure referred to below in respect of cycles of positive and/or negative pressure.

To clarify there are two forms of stress generally envisaged as being useful, i.e. those achieved by a slow cycling of pressure, and those achieved by a more rapid pulsing of pressures. The range of pressure in a "cycle" is typically significantly greater than that of a "pulse". An analogy is a carrier wave (the cycle) containing the pulse superimposed upon it.

Regularly or randomly pulsing any pressure applied to the wound may be effected essentially as described hereinbefore in connection with the variation of the positive and/or negative pressure applied to the wound. Again, such regular or random pulsing of the positive and/or negative pressure applied to the wound may be effected by conventional process control devices and/or software.

Such pulsing of any pressure applied to the wound may be applied as an amplitude modulation of the positive and/or negative pressure applied to the wound bed and optionally tissue surrounding the wound, which in turn may be held constant, but more usually is varied, preferably cyclically, either randomly or regularly (i.e. the carrier wave referred to above may in fact be a constant positive or negative pressure), but this is generally less preferred.

Where the levels of such pressure above or below atmospheric are held constant, this is often achieved in the present apparatus, where appropriate, by use of a control device that can regulate the pressure in the wound dressing by bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or programme.

This often results in any device for moving fluid through the wound that is downstream of the dressing and that applies an overall negative pressure in the wound space, e.g. a vacuum pump, pumping a heterogeneous mixture of liquid wound exudate and irrigant from the wound dressing with bleed gases, such as air and nitrogen. This can result in pulsing of any pressure applied to the wound.

The pumping rate and the dimensions of the offtake and/or supply tubes may be adjusted to maintain the desired balance of pulsing pressure amplitude and frequencies on the wound.

Preferably such a system is a conventional automated, programmable system which can maintain the appropriate pulse regimen to the wound.

Stimulus to the wound bed and optionally tissue surrounding the wound by applying an optionally varying positive and/or negative pressure and agitation of the wound bed to stimulate the cells by regularly or randomly pulsing any pressure applied to the wound are mutually compatible. They may, as appropriate, be applied alone or together.

Thus, an embodiment of the apparatus for irrigating, stressing and/or cleansing wounds of the present invention is characterised in that it comprises means for supplying optionally varying positive and/or negative pressure, which is optionally pulsed, to a wound bed and optionally tissue surrounding the wound for the stimulation of the healing of the wound.

As noted hereinbefore, in the present invention in this aspect, the positive and/or negative pressure on the wound bed and/or the fluid thereover and optionally tissue surrounding the wound may be constant, but more usually is varied, preferably cyclically, either randomly or regularly. Where the pressure on the wound bed and/or the fluid thereover and optionally tissue surrounding is varied, it may be a varying positive or negative pressure, or it may as appropriate vary from positive to negative or vice versa, again preferably cyclically, and either randomly or regularly. It may vary about a constant positive or negative baseline pressure, or less usually about a varying baseline pressure. Examples of maximum levels of such pressure above and below atmospheric include 50% atm. e.g. between 5 and 40% atm., e.g. between 15 and 35% atm.

Examples of suitable frequencies of such regular cycles of pressure for the stimulation of the healing of wounds include 1 to 48 per 24 hr, such as 12 to 24 per 24 hr, e.g. 2 to 1 per hr.

Examples of suitable waveforms of such cycles either regularly or randomly for the stimulation of the healing of wounds include curved, e.g. sinusoidal, random white noise and sawtooth for higher frequencies, and usually square for lower frequencies.

Examples of suitable frequencies of regular pulses for the stimulation of the healing of wounds include 1 to 3000 per min (0.016-50 Hz), e.g. 30 to 60 per min, e.g. 3 to 20 per min, i.e. 0.05 to 0.33 Hz, such as 5 to 10 per min.

Such pulses may be varying positive or negative pressure pulses, or they may as appropriate vary from positive to negative or vice versa, again preferably cyclically, and either randomly or regularly.

They may vary about a constant positive or negative baseline pressure or about a varying baseline pressure. Examples of maximum amplitudes for such pulses are up to 10 mm Hg above and below the constant positive or negative baseline pressure, e.g. up to 7 mm Hg or up to 3 mm Hg.

Examples of suitable waveforms of such pulses either regularly or randomly for the stimulation of the healing of wounds include curved, e.g. sinusoidal, random white noise sawtooth, square and a systolic-diastolic asymmetric sawtooth.

Where the amplitude of regular cycles of pressure is modulated by superimposed regular pulses for the stimulation of the healing of wounds, examples of suitable frequencies of the combination include those where the carrier frequency is 1 to 48 per 24 hours and the superimposed frequency of the pressure pulses is 1 to 0.05 Hz, both with the respective amplitudes noted above.

Examples of suitable waveforms of the cycles and the superimposed pulses may be regular or random and include curved, e.g. sinusoidal, random white noise, sawtooth, square and a systolic-diastolic asymmetric sawtooth.

Examples of means for applying an optionally varying positive and/or negative pressure at any appropriate point for stressing the wound and/or regularly or randomly pulsing any pressure applied to the wound for promoting wound healing, whether applied alone or together, include a wound dressing as hereinbefore defined that comprises one or more expandable and contractible modules capable of applying pressure to the wound bed and optionally tissue surrounding the wound at any appropriate point for stressing the wound.

Examples of other suitable means of applying mechanical stimulus to the wound by optionally varying positive and/or negative pressure include a magnetic fluid in a chamber or other hollow structure under the backing layer of the dressing in contact with the wound bed and/or the fluid thereover. A regularly or randomly (preferably cyclically) varying and/or pulsing external magnetic field is applied to the magnetic fluid. However, such means are generally less favoured.

Thus, one favoured embodiment of the apparatus for irrigating, stressing and/or cleansing wounds is characterised in that it comprises a wound dressing as hereinbefore defined that comprises one or more expandable and contractible modules. Such a module is capable of applying pressure to the wound bed and optionally tissue surrounding the wound at any appropriate point for stressing the wound. It should be capable of maintaining the pressure on the wound bed and/or the fluid thereover and optionally tissue surrounding the wound at a constant level, but more usually it should be capable of regularly or randomly (preferably cyclically) varying and/or pulsing the pressure applied to the wound, all at or near an appropriate, desired level of stress to the wound bed and optionally tissue surrounding the wound, to an appropriate, desired programme while moving fluid over the wound bed at an appropriate, desired rate.

Examples of suitable modules capable of applying pressure to the wound bed at any appropriate point for stressing the wound include a module in the wound dressing may be made of a polymer that can be electrically stimulated to change shape repeatedly at appropriate frequencies.

A preferred module is a fluid-inflatable body that lies in the wound in use.

Thus, one favoured embodiment of the apparatus for irrigating, stressing and/or cleansing wounds is characterised in that it comprises a wound dressing as hereinbefore defined that comprises one or more fluid-inflatable modules capable of applying pressure to the wound bed at any appropriate point for stressing the wound.

This is capable of maintaining the pressure on the wound bed and/or the fluid thereover at a constant level, but more usually it is also capable of regularly or randomly (preferably cyclically) varying and/or pulsing the pressure applied to the wound, all at or near an appropriate, desired level of stress to the wound bed, to an appropriate, desired programme while moving fluid over the wound bed The module or modules is/are (usually cyclically) inflated and deflated by admitting and releasing fluid.

Once the inflatable body has been inflated, it may be deflated as appropriate or desired, and then reinflated to again apply a positive pressure to the wound, and the cycle may be repeated as appropriate or desired.

Alternatively, it may be partially filled with an elastically resilient material, such as an elastomeric foam, that in its rest state is capable of applying a working pressure to the wound bed. The body may then be deflated as appropriate or desired, and then reinflated under the action of its filler material to again apply a positive pressure to the wound, and the cycle may be repeated as appropriate or desired.

Examples of forms of the body that are suitable such expandable and contractible modules capable of applying pressure to the wound bed at any appropriate point for stressing the wound include fluid-inflatable fillers and fluid-inflatable irrigant inlet manifolds comprised in the dressing, as described hereinafter in greater detail.

Where the module is a fluid-inflatable filler, examples of suitable fluids include gases, such as air and nitrogen; liquids, such as water and saline; gas in liquid aerosols; and gels such as those described in greater detail hereinafter. Preferred fluids include gases, such as air or nitrogen.

Where the module is a fluid-inflatable irrigant inlet manifold comprised in the dressing as described hereinafter in greater detail, it will be stimulated to change shape as appropriate and optionally at desired frequencies by inflation with irrigant, followed as desired by deflation.

Examples of Both are Included Hereinafter.

Examples of such fillers include a substantially flat film, sheet or membrane, defining a chamber, pouch or other structure of the backing layer, e.g. of polymer film, which can contain the inflation fluid.

It is provided with an inflation device for moving inflation fluid to the filler, and is connected to it by an inflation tube which communicates with its internal space. The inflation device may also serve as a deflation device for moving inflation fluid from the filler, and the inflation tube also serves as a deflation tube.

Alternatively or additionally, where appropriate the filler as hereinbefore defined may have a deflation pipe and a bleed valve to waste, e.g. to a collection bag if a non-gaseous fluid is used. The inflation device for moving inflation fluid then only serves as an inflation device to apply a positive pressure on the wound bed.

Less usually, the filler may have an inflation device and a deflation device.

Where it lies under the backing layer of the wound dressing of the apparatus of the invention, the inflation tube may run to the filler within the wound under the wound-facing face of the wound dressing.

However, the inflation tube may be connected to an inflation pipe that passes through the wound-facing face of the backing layer, the point at which the inflation pipe passes through the wound-facing face forming a relatively fluid-tight seal.

The inflation pipe may be in the form of an aperture, such as a funnel hole, opening, orifice, luer, slot or port for connection as a female member respectively to a mating end of the inflation tube (optionally or as necessary via means for forming a tube, pipe or hose, or nozzle).

Where the pipe passes through, rather than under the backing layer, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of the inflation tube.

The components may be a push, snap or twist-lock fit with each other.

The minimum calibre of the inflation tube and pipe must be sufficient for them to permit as rapid inflation and deflation of the filler as is desired.

Suitably the range of cross-dimensions of the bore (i.e. calibre) may be 0.5 to 6 mm, e.g. 1.5 to 2 mm.

Each should be resiliently flexible, and preferably soft with good conformability. This can be done for example by forming it of a suitable material, e.g. a resilient thermoplastic.

Examples of suitable inflation device for moving fluid into the filler include pumps. As noted above, the inflation device may also serve as a deflation device for moving inflation fluid from the filler, and the inflation tube also serves as a deflation tube. In such case, the pump must be a reversible pump used to increase and decrease the pressure on the wound bed as desired.

Subject to this consideration, the type and/or capacity of the device will also be largely determined by the appropriate or desired positive or negative pressure to the wound bed, the nature of the fluid, i.e. whether it is a gas, such as air and nitrogen; a liquid, such as water and saline; a gas in liquid aerosol; or a gel;

the desired frequencies and waveforms of such cycles either regularly or randomly.

The following types of pump may be used to apply positive pressure, as desired to the filler through an inflation tube which communicates with its internal space:

Reciprocating Pumps, such as:

Syringe or piston pumps—providing high pressure and high accuracy;

Diaphragm pumps—where pulsations of one or two flexible diaphragms displace liquid while check valves control the direction of the fluid flow e.g. preferably a small portable diaphragm pump.

and

Rotary pumps, such as:

Centrifugal pumps—with rotating vaned disk attached to a drive shaft moving fluid without pulsation as it spins. The outlet can be restricted without damaging the pump.

Peristaltic pumps—with rollers on a rotor acting on fluid in a tube, e.g. preferably a small portable peristaltic pump.

Of these, only piston pumps and rotary pumps, such as centrifugal pumps and peristaltic pumps are readily reversible pumps that may be used to increase and decrease the pressure on the wound bed as desired.

Subject to this consideration, preferred reversible pumps include a small portable peristaltic pump.

Preferred non-reversible pumps to be used with a bleed valve to the filler then include a small portable syringe pump (which is often used once and then disposed of) or small portable diaphragm pump, e.g. a sphygmometric pump.

Where the module is a fluid-inflatable irrigant inlet manifold comprised in the dressing as described herein after in greater detail, it will be stimulated to change shape as appropriate and optionally at desired frequencies by inflation with irrigant, followed as desired by partial deflation. It should be noted that the use of such a system is more suited to a simultaneous system but could be applied to a sequential (i.e. fill/empty cycle) system. When the manifold is inflated it will influence the pressure applied to the surface of the wound, and when deflated the pressure will be reduced (i.e. relative to the baseline of the system).

The device for moving fluid through the wound is used to move irrigant to inflate the inlet manifold and apply a positive pressure to the wound bed. As noted hereinafter, the device may suitably be a pump.

As noted hereinbefore, the pressure on the wound bed may be constant, but may be varied, preferably cyclically, either randomly or regularly.

To achieve this, the present apparatus, where appropriate, comprises a system that can regulate the pump output to the inlet manifold in the wound dressing.

Preferably such a system is a conventional automated, programmable system which can maintain the wound at or near an appropriate, desired flow stress to the wound bed to an appropriate, desired programme while moving fluid over the wound bed.

As noted hereinbefore, stimulation of the healing of wounds in the present invention may also be effected by regularly or randomly pulsing a pressure applied to the wound at any appropriate point for this purpose.

Such pulsed flow across the wound may be provided by some types of the device for moving fluid through the wound. Certain diaphragm pumps described hereinafter in greater detail will be appropriate for this purpose, as are certain peristaltic pumps, and an electromechanical oscillator directly coupled to the wound dressing, would also be suitable.

Suitable materials for such modules (i.e. fillers, manifolds etc) of any type include synthetic polymeric materials that do not absorb aqueous fluids, such as polyolefins, polysiloxanes and polyesters. They may be hydrophilic, and thus also include hydrophilic polyurethanes. They also include thermoplastic elastomers and elastomer blends, for example copolymers, such as ethyl vinyl acetate polystyrene and elastomeric polyurethane formed by solution casting.

Where the present invention involves simultaneous irrigation/aspiration it provides several further advantages.

One is that application of an irrigant to a wound under simultaneous aspiration creates a wound environment that is exposed to the continuous beneficial effects of both aspects of the therapy for wound healing, as opposed to the sequential intermittent application of irrigant flow and aspiration in known aspirating and/or irrigating apparatus. The latter result in less than optimum performance of the body's own tissue healing processes, and slower healing and/or weaker tissue growth that does not have a strong three-dimensional structure adhering well to and growing from the wound bed. This is a significant disadvantage, in particular in chronic wounds.

Such a system is particularly suited for removing materials deleterious to wound healing with the wound exudate, reducing bacterial load, combating peri-wound oedema and encouraging the formation of wound bed granulation tissue.

Preferred embodiments of the apparatus of the present invention for aspirating, irrigating and/or cleansing chronic wounds apply a milder negative pressure than in conventional negative pressure therapy (which is too aggressive for the fragile tissues of many such wounds). This leads to increased patient comfort, and lessens the risk of inflammation of the wound.

The removal of wound exudate in a given time period of application of the simultaneous irrigate and/or aspirate therapy will normally be more effective and/or faster than with a conventional sequential intermittent aspiration and/or irrigation therapy.

Even more desirably, since simultaneous aspiration and irrigation is applied to the wound, wound exudate and materials deleterious to wound healing (such as bacteria and debris, and iron II and iron III and for chronic wounds proteases) will not pool on the wound bed and hinder wound healing, especially in a highly exuding wound. This is especially important in chronic wounds.

The resulting mixed exudate-irrigant fluid will usually be of relatively lower viscosity.

Because simultaneous aspiration and irrigation of the wound provides continuous removal at a constant relatively high speed, the fluid does not have to be accelerated cyclically from rest, and will be easier to shift than with known forms of aspiration and/or irrigation therapy systems with a conventional sequential aspirate—irrigate—dwell cycle. This will thus exert a greater net effect on the removal of adherent bacteria and debris.

This is especially the case in those embodiments of the apparatus of the present invention for aspirating, irrigating and/or cleansing wounds where there is an inlet manifold (as described below).

An inlet manifold generally covers and contacts a significant area, preferably most, of the wound bed with openings that deliver the fluid directly to the wound bed over an extended area.

It will be seen that the balance of fluid between fluid aspirated from the wound and irrigant supplied to the wound from the irrigant reservoir may provide a predetermined steady state concentration equilibrium of materials beneficial in promoting wound healing over the wound bed. Simultaneous aspiration of wound fluid and irrigation at a controlled flow rate aids in the attainment and maintenance of this equilibrium The apparatus for irrigating and/or aspirating wounds of the present invention may be used cyclically and/or with reversal of flow.

Preferably the present apparatus for aspirating, irrigating and/or cleansing wounds is a conventionally automated, programmable system which can cleanse the wound with minimal supervision.

The means for providing simultaneous aspiration and irrigation of the wound often comprise:
- a (first) device for moving fluid through the wound applied to fluid downstream of and away from the wound dressing, in combination with at least one of
- a second device for moving fluid through the wound applied to the irrigant in the fluid supply tube upstream of and towards the wound dressing;

means for aspirate flow regulation, connected to a fluid offtake tube; and
means for supply flow regulation, connected to a fluid supply tube.

The (first) device will generally apply negative pressure (i.e. below-atmospheric pressure or vacuum) to the wound bed. It may be applied to the aspirate in the fluid offtake tube downstream of and away from the wound dressing.

Alternatively or additionally, where appropriate, the aspirate in the fluid offtake tube downstream of the wound dressing may be aspirated into a collection vessel, and the first device may act on fluid such as air from the collection vessel. This prevents contact of the device with the aspirate.

The (first) device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve.

Alternatively, where appropriate the (first) device for moving fluid through the wound may be a variable-throughput device, such as a variable-speed pump, downstream of the wound dressing, thus effectively forming a combination of a (first) device for moving fluid through the wound with means for aspirate flow regulation and/or means for supply flow regulation in a single integer.

The (first) device for moving fluid through the wound will often be a pump of any of the types set out below, or a piped supply of vacuum, applied to fluid downstream of and away from the wound dressing.

The Following Types of Pump May be Used as the (First) Device:

Reciprocating Pumps, such as:

Piston Pumps—where pistons pump fluids through check valves, in particular for positive and/or negative pressure on the wound bed; and Diaphragm Pumps—where pulsations of one or two flexible diaphragms displace liquid with check valves.

and

Rotary Pumps, such as:

Progressing cavity pumps—with a cooperating screw rotor and stator, in particular for higher-viscosity and particulate-filled exudate; and Vacuum pumps—with pressure regulators.

The (first) device may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Where the pump is a diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

Where any second device is applied to the fluid in the fluid supply tube upstream of and towards the wound dressing, it will usually apply positive pressure (i.e. above-atmospheric pressure) to the wound bed.

As with the (first) device, it may be a fixed-throughput device, such as a fixed-speed pump, which will usually require a discrete means for supply flow regulation, connected to a fluid supply tube, e.g. a regulator, such as a rotary valve.

Alternatively, where appropriate the second device for moving irrigant fluid to the wound may be a variable-throughput device, such as a variable-speed pump, upstream of the wound dressing, thus effectively forming a combination of a second device for moving fluid through the wound with means for supply flow regulation in a single integer.

The second device for moving fluid through the wound will often be a pump of any of the following types applied to the irrigant in the fluid supply tube upstream of and towards the wound dressing. It may be a fixed-speed pump, with (as above) a discrete means for supply flow regulation, connected to a fluid supply tube, e.g. a regulator, such as a rotary valve. Alternatively, where appropriate the pump may be a variable-throughput or variable-speed pump.

The Following Types of Pump May be Used as the Second Device:

Reciprocating Pumps, such as:

Shuttle Pumps—with an oscillating shuttle mechanism to move fluids at rates from 2 to 50 ml per minute and Rotary Pumps, such as:

Centrifugal pumps Flexible impeller pumps—where elastomeric impeller traps fluid between impeller blades and a moulded housing that sweeps fluid through the pump housing.

Peristaltic pumps—with peripheral rollers on rotor arms acting on a flexible fluid aspiration tube to urge fluid current flow in the tube in the direction of the rotor.

Rotary vane pumps—with rotating vaned disk attached to a drive shaft moving fluid without pulsation as it spins. The outlet can be restricted without damaging the pump.

The second device may be a peristaltic pump, e.g. preferably a small portable peristaltic pump. This is a preferred type of pump, in order in particular to reduce or eliminate contact of internal surfaces and moving parts of the pump with irrigant, and for ease of cleaning.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

Each such pump of any these types may also suitably be one that is capable of pulsed, continuous, variable and/or automated and/or programmable fluid movement. Less usually and less preferably, each such pump of any these types will be reversible.

As above, the means for supply flow regulation may be a regulator, such as a rotary valve. This is connected between two parts of a fluid supply tube, such that the desired supply flow regulation is achieved.

If there are two or more inlet pipes, these may be connected to a single fluid supply tube with a single regulator, or to first, second, etc. fluid supply tubes, respectively having a first regulator, a second regulator, etc., e.g. a valve or other control device for admitting fluids into the wound.

As above, the means for aspirate flow regulation may be similarly provided in a form in which concomitant aspirate flow regulation is possible. It may be a regulator, such as a valve or other control device, e.g. a rotary valve.

Multiple offtake tubes may be similarly provided with single or multiple regulators, all for aspiration of fluids from the apparatus, e.g. to a aspirate collection vessel, such as a collection bag.

If there is no second device for moving fluid through the wound applied to the irrigant in the fluid supply tube upstream of and towards the wound dressing, it is only possible to apply a negative pressure to the wound, by means of the device for moving fluid through the wound applied to the aspirate in the fluid offtake tube downstream of and away from the wound dressing.

Operation may e.g. be carried out at a negative pressure of up to 50% atm., typically at a low negative pressure of up to 20% atm., more usually up to 10% atm. at the wound, as is described hereinafter.

Examples of suitable and preferred (first) devices include as described hereinbefore, a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Alternatively, if it is desired to apply a net positive pressure to the wound, the means for providing simultaneous aspiration and irrigation of the wound must comprise not only
   a first device for moving fluid through the wound applied to the aspirate in the fluid offtake tube downstream of and away from the wound dressing, but also
   a second device for moving fluid through the wound applied to the irrigant in the fluid supply tube upstream of and towards the wound dressing.

Operation may then e.g. be carried out at a positive pressure of up to 50% atm., typically at a low positive pressure of up to 20% atm., more usually up to 10% atm. at the wound, as is described hereinafter.

Examples of suitable and preferred first devices include those types of pump that are so described hereinbefore in relation to the first device. This may be a diaphragm pump, e.g. preferably a small portable diaphragm pump.

Examples of suitable and preferred second devices include those types of pump that are so described hereinbefore in relation to the first device. This may be a peristaltic pump, e.g. a miniature peristaltic pump.

It is of course equally possible to apply a negative pressure to the wound, by means of such a combination of;
   a first device for moving fluid through the wound applied to the aspirate in the fluid offtake tube downstream of and away from the wound dressing, and
   a second device for moving fluid through the wound applied to the irrigant in the fluid supply tube upstream of and towards the wound dressing;
optionally with
   means for supply flow regulation, connected to a fluid supply tube; and/or
   means for aspirate flow regulation, connected to a fluid offtake tube.

Indeed, as noted below in this regard, preferred embodiments of the apparatus of this first aspect of the present invention for aspirating, irrigating and/or cleansing chronic wounds that apply a negative pressure include such types of combination of;
   a first device, e.g. a diaphragm pump, e.g. preferably a small portable diaphragm pump, and
   a second device, e.g. a peristaltic pump, preferably a miniature peristaltic pump.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

The higher end of the ranges of % positive and negative pressure noted above are potentially more suitable for hospital use, where they may only be used safely under professional supervision. The lower end is potentially more suitable for home use, where relatively high % positive and negative pressures cannot be used safely without professional supervision, or for field hospital use.

In each case, the pressure on the wound may be held constant throughout the desired length of therapy, or may be varied cyclically in a desired positive or negative pressure regime.

As noted above, when it is desired to apply a negative pressure to the wound, it is preferred that the means for providing simultaneous aspiration and irrigation of the wound comprise not only a (first) device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Accordingly, one embodiment of the apparatus for irrigating, cleansing and/or aspirating wounds of the present invention is characterised in the means for providing simultaneous aspiration and irrigation of the wound comprises:

a (first) device for moving fluid through the wound applied to fluid downstream of and away from the wound dressing, and a second device for moving fluid through the wound applied to the irrigant in the fluid supply tube upstream of and towards the wound dressing, and in combination with at least one of means for supply flow regulation, connected to a fluid supply tube, and means for aspirate flow regulation, connected to a fluid offtake tube.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

This combination of a device for moving fluid through the wound applied to the aspirate in the fluid offtake tube downstream of and away from the wound dressing, and a device for moving fluid through the wound applied to the fluid in the fluid supply tube upstream of and towards the wound dressing, may be used to apply an overall positive or negative, or even zero pressure to the wound.

At least one body in the flow path to, over and from the wound bed should have sufficient resilience against the pressure to allow any significant compression or decompression of the fluid occur.

Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials.

It will be seen that the balance of fluid between aspirated fluid from the wound and irrigant supplied to the wound from the fluid reservoir will thus be largely determined by a means for providing simultaneous aspiration and irrigation of the wound which may be a system comprising:

a) means for aspirate flow regulation and/or a device for moving fluid through the wound applied to fluid downstream of and away from the wound dressing, and b) means for supply flow regulation and/or a device for moving fluid through the wound applied to the fluid in the fluid supply tube upstream of and towards the wound dressing.

The same means may be used to apply an overall positive or negative, or even neutral pressure to the wound. The means may also be used to vary the pressure in the wound dressing (e.g. via a manifold) to apply stress to the wound bed and optionally areas surrounding the wound.

The appropriate flow rate through the supply tube will depend on a number of factors, such as:

the viscosity and consistency of each of the irrigant, exudate and mixed exudate-irrigant fluid, and any changes as the wound heals;

the level of negative pressure on the wound bed;

whether the irrigant in the fluid supply tube upstream of and into the wound dressing is under positive pressure, and the level of such pressure;

the level of any pressure drop between the irrigant in the fluid supply tube upstream of the wound dressing and the wound bed, such as across a porous element, e.g. a membrane wound contact layer on the lower surface of an inlet manifold that delivers the fluid directly to the wound bed;

the depth and/or capacity of the wound; and the power consumption needed for a given desired fluid volume flow rate of irrigant and/or wound exudate through the wound.

The dressing may comprise an inlet manifold (as described in further detail hereinafter) that covers and contacts a significant area, preferably most, of the wound bed with openings that deliver the fluid directly to the wound bed over an extended area, in the form of one or more inflatable hollow bodies defined by a film sheet or membrane. In general a manifold will cover 50% of the wound preferably 75% or more, though it is possible that it may cover a smaller area of the wound.

The (usually small) positive pressure above atmospheric from the irrigation device when both devices are running together should be sufficient to inflate the manifold.

The desired fluid volume flow rate of irrigant and/or wound exudate is preferably that for optimum performance of the wound healing process.

The flow rate will usually be in the range of 1 to 1500 ml/hr, such as 5 to 1000 ml/hr, e.g. 15 to 300 ml/hr, such as 35 to 200 ml/hr through the supply tube. The flow rate through the wound may be held constant throughout the desired length of therapy, or may be varied cyclically in a desired flow rate regime.

In practice, the offtake rate of flow of total irrigant and/or wound exudate will generally be of the order of 1 to 2000, e.g. 35 to 300 ml/24 hr/cm$^2$, where the cm$^2$ refers to the wound area, depending on whether the wound is in a highly exuding state.

In practice, the rate of exudate flow is typically only of the order of up to 75 microliters/cm$^2$/hr (where cm$^2$ refers to the wound area), and the fluid can be highly mobile or not, depending on the level of proteases present). Exudate levels drop and consistency changes as the wound heals, e.g. to a level for the same wound that equates to 12.5-25 microliters/cm$^2$/hr.

It will be apparent that the aspirated fluid from the wound will typically contain a preponderance of irrigant from the fluid reservoir over wound exudate.

The necessary adjustments to maintain the desired balance of fluid by means of a) the means for aspirate flow regulation and/or downstream device, and b) the means for supply flow regulation and/or upstream device for moving fluid will be apparent to the skilled person, bearing in mind that, as noted above, either of the first device and the second device may be:

- a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or
- a variable-throughput device, such as a variable-speed pump, downstream of the wound dressing, thus effectively forming a combination of a (first) device for moving fluid through the wound with means for aspirate flow regulation and/or means for supply flow regulation in a single integer.

The type and/or capacity of a suitable first and/or second device will be largely determined by a) the appropriate or desired fluid volume flow rate of irrigant and/or wound exudate from the wound, and b) whether it is appropriate or desired to apply a positive or negative pressure to the wound bed, and the level of such pressure to the wound bed for optimum performance of the wound healing process, and c) by factors such as portability, power consumption and isolation from contamination.

As noted above, when it is desired to apply a negative pressure to the wound with the apparatus of the present invention for aspirating, irrigating and/or cleansing wounds to provide simultaneous aspiration and irrigation of the wound, the means for providing simultaneous aspiration and irrigation of the wound may comprise

- a single device for moving fluid through the wound applied to the aspirate in the fluid offtake tube downstream of and away from the wound dressing or in combination with at least one of:
- means for supply flow regulation, connected to a fluid supply tube, and
- means for aspirate flow regulation, connected to a fluid offtake tube.

As noted above, the device may be a fixed-throughput device or a variable-throughput device.

In a further aspect the present invention provides a method of operation of an apparatus for aspirating, irrigating and/or cleansing wounds said method comprising the steps of:

a) providing an apparatus as set out above;
b) applying the wound dressing to the wound;
c) conforming the backing layer of the wound dressing to the shape of the bodily part in which the wound is to form a relatively fluid tight seal or closure;
d) activating the at least one device for moving fluid through the wound dressing to the wound and/or from the wound to cause irrigant to move to the wound; and
e) activating the means for stressing the wound bed and optionally tissue surrounding the wound to apply a stress to the wound bed.

In a preferred embodiment the apparatus has at least one inlet pipe and at least one outlet pipe, each of which passes through and/or under the wound-facing face. Such an embodiment allows for a method simultaneous and/or sequential irrigation/aspiration of the wound. In such an embodiment step d) of the method comprises activating the at least one device of moving fluid through the wound dressing to move fluid (irrigant) through the at least one inlet and to move fluid (aspirate) out of the at least one outlet pipe.

In a preferred embodiment the irrigant is moved to the wound via the inlet pipe and aspirate removed from the outlet pipe simultaneously, i.e. simultaneous irrigation/aspiration. This may be carried out for substantially the entirety of the treatment of the wound, or alternately for portions of the treatment as desired.

Such an embodiment is also suitable for sequential (fill/empty) operation, and thus a method wherein sequential operation is carried out forms an alternative embodiment of the invention. In such an embodiment irrigation would be ceased by ceasing the device moving fluid through the at least one inlet and activating a device to move fluid from the wound through the outlet.

Suitable flow rates, parameters for operation of the means for applying stress and for operation of the apparatus in general are set out above. Further details are given below.

The operation of a typical apparatus of this type for simultaneous aspiration and irrigation of a wound at a low negative pressure of up to 20% atm., more usually up to 10% atm. at the wound, with one pump may involve the following steps. As mentioned previously, the application of negative pressure has beneficial effects in wound healing.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

The means for supply flow regulation, connected to a fluid supply tube, such as a regulator, such as a rotary valve, is usually closed, and the means for aspirate flow regulation (if any), connected to a fluid offtake tube, is opened.

The aspiration pump (i.e. first device) is started and run to give a negative pressure of up to 50% atm., more usually up to 20% atm., e.g. up to 10% atm. to be applied to the interior of the dressing and the wound.

The means for fluid supply regulation is opened and is then adjusted, and/or where the aspiration pump is a variable-speed pump, downstream of the wound dressing, that is adjusted, to maintain the desired balance of fluid at a controlled nominal flow rate and to maintain the desired negative pressure in the interior of the wound dressing.

The means of applying stress is then activated. Typically the means for applying stress comprises at least one expandable or contractible module capable of applying pressure to the wound bed. In one embodiment such a module comprises an inflatable body which lies within the wound in use. The inflatable body may be used to apply a constant pressure (and hence stress) to the wound or, preferably, may be used to apply a cyclical pressure. The module may be inflated and deflated be introducing and removing fluid to the body. Further details of suitable modules and their operation are given above.

The apparatus is then run for the desired length of therapy and with the desired negative pressure and stress regime. After this period, the aspiration pump is stopped.

The operation of a typical apparatus for simultaneous aspiration and irrigation of a wound at a low negative pressure of up to 20% atm., more usually up to 10% atm. at the wound, with two pumps may involve the following steps.

The necessary changes where the mode of operation for a net positive pressure of e.g. up to 15% atm., more usually up to 10% atm. at the wound will be apparent to the skilled person.

A typical apparatus for simultaneous aspiration and irrigation of a wound at a low negative pressure of up to 20% atm., more usually up to 10% atm. at the wound comprises means for providing simultaneous aspiration and irrigation of the wound which is a combination of a) a first device for moving fluid through the wound applied to the aspirate in the fluid offtake tube downstream of and away from the wound dressing, with optional means for aspirate flow regulation, connected to a fluid offtake tube; and
b) a second device for moving fluid through the wound applied to the irrigant in the fluid supply tube upstream of and towards the wound dressing, with optional means for supply flow regulation, connected to a fluid supply tube.

As noted above, either device may be a fixed-throughput device or a variable-throughput device.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

Any means for supply flow regulation, connected to a fluid supply tube, such as a regulator, such as a rotary valve, is usually closed, and any means for aspirate flow regulation, connected to a fluid offtake tube, is opened.

The aspiration pump is started and run to apply a negative pressure of up to 50% atm., more usually up to 20% atm., e.g. up to 10% atm., to the interior of the dressing and the wound.

The irrigation pump is then started, so that both pumps are running together, and any means for supply flow regulation is opened.

The irrigation pump flow rate and any means for fluid supply regulation are then adjusted and/or where the aspiration pump and/or the irrigation pump is a variable-speed pump, either or both is/are adjusted, to maintain the desired balance of fluid at a controlled nominal flow rate and to maintain the desired negative pressure in the interior of the wound dressing.

The means for applying stress is then activated, as described above.

The apparatus is then run for the desired length of therapy and with the desired pressure regime. After this period, the irrigation pump is stopped, shortly followed by the aspiration pump.

In all embodiments of the apparatus of the present invention for aspirating, irrigating and/or cleansing wounds, a particular advantage is the tendency of the wound dressing to conform to the shape of the bodily part to which it is applied.

The term 'relatively fluid-tight seal or closure' is used herein to indicate one which is fluid- and microbe-impermeable and permits a positive or negative pressure of up to 50% atm., more usually up to 20% atm., e.g. up to 10% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound. Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound. This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable). This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide securing means for forming and maintaining such a seal or closure over the wound against such positive pressure on the wound, to act at peripheral points for this purpose. Examples of such securing means include light switchable adhesives, as above, to secure the dressing in place to prevent leakage. Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such securing means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheaths, wraps, stockings and hose that are a compressive fit over a limb wound to apply suitable pressure to it when the therapy is applied in this way.

Such securing means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such securing means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The securing means and the dressing may be separate structures, permanently unattached to each other.

In a more suitable layout for higher positive pressures on the wound, a stiff flange or lip extends around the periphery of the proximal face of the backing layer of the wound dressing. The flange or lip is concave on its proximal face to define a peripheral channel or conduit. It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound. The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of a fluid tube and/or fluid supply tube (optionally or as necessary via means for forming a tube, pipe or hose, or nozzle, hole, opening, orifice, luer, slot or port for connection as a male member respectively to a mating end of a fluid tube and/or fluid supply tube (optionally or as necessary via means for supply flow regulation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer. In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

Where a simple pipe is used to supply the irrigant to the wound, this may not provide a system to distribute irrigant over a sufficient functional surface area to irrigate the wound at a practical rate to be suitable for use, in particular in chronic wound aspiration and irrigation, which may contain relatively high concentrations of materials that are deleterious to wound healing.

It may be advantageous to provide a system where wound irrigant may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the aspirating fluid directly to the wound bed via the apertures. Similarly, there is optionally an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the aspirating fluid directly to the wound bed or outlet pipe or collects the fluid directly from the wound respectively. It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix.

Other suitable layouts for shallower wounds include one which have blind-bore, perforated inlet pipe or outlet pipe manifolds that aspirate fluid in the wound when the dressing is in use.

One or both of these may be such a form, the other may be, e.g. one or more straight blind-bore, perforated radial tubes, pipes or nozzles.

A preferred form of inlet pipe (or less usually) outlet pipe manifold that delivers the aspirating fluid directly to the wound bed or collects the fluid directly from the wound respectively is one that comprise one or more conformable hollow bodies defined by a film, sheet or membrane, such as a bag, chamber, pouch or other structure, filled with the irrigant (or less usually aspirate) from the wound, passing through perforations, apertures, holes, openings, orifices, slits or slots in the film, sheet or membrane defining the hollow body or hollow bodies.

These may be of small cross-dimension, so that they may then effectively form microperforations, microapertures or pores in a permeable integer, for example the polymer film, sheet or membrane.

This type of manifold for irrigation (more usually) provides the highest uniformity in the flow distribution of irrigant over the wound at a practical rate to be suitable for use, in particular in chronic wound aspiration and irrigation, and hence to provide a system where materials that are beneficial in promoting wound healing, such as growth factors, cell matrix components, and other physiologically active components of the exudate from a wound, are distributed more evenly under the dressing over the wound bed.

This type of manifold for irrigation (more usually) is noted below with regard to wound fillers under the backing layer, since it is a resiliently flexible, e.g. elastomeric, and soft, structure with good conformability to wound shape.

It is urged by its own resilience against the backing layer to apply gentle pressure on the wound bed, and is therefore also capable of acting as a wound filler. The film, sheet or membrane, often has a (generally uniform) thickness similar to that of films or sheets used in conventional wound dressing backing layers.

Another suitable layout is one in which an inlet pipe and/or outlet pipe manifold that delivers the aspirating fluid directly to the wound bed or collects the fluid directly from the wound respectively via inlet and/or outlet tubes, pipes or tubules, and the inlet manifold and/or outlet manifold is formed by slots in layers permanently attached to each other in a stack, and the inlet and/or outlet tubes, pipes or tubules are formed by apertures through layers permanently attached to each other in a stack.

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape. It is urged by its own resilience against the backing layer to apply gentle pressure on the wound bed. The wound filler may be integral with the other components of the dressing, in particular the backing layer. Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic.

Preferred materials for the fillers include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials.

Examples also include aerosol foams, where the gaseous phase of the aerosol system is air or an inert gas, such as nitrogen or argon, more usually air, at a small positive pressure above atmospheric; and solid particulates, such as plastics crumbs.

In an alternative embodiment the filler of the apparatus can conveniently be an expandable or contractible module which is the means to apply stress to the wound bed. In one preferred embodiment the module comprises an inflatable body, e.g. an inflatable pouch or bag.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure.

It has apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the aspirating or irrigating fluid in the apparatus.

The hollow body or each of the hollow bodies then effectively forms an inlet pipe or outlet pipe manifold that delivers the aspirating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the aspirating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

The wound filler under the backing layer effectively may form an (or be formed by) inlet pipe or outlet pipe manifold.

If not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler maybe an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that aspirate fluid in the wound when the dressing is in use, that are described hereinbefore, may be used under a wound filler under the backing layer.

In brief, suitable layouts include ones where one or both manifolds are annular or toroidal (regular, e.g. elliptical or circular or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid tube and the fluid supply tube, etc. may be of conventional type, e.g. of elliptical or circular cross-section, and may suitably have a uniform cylindrical bore, channel, conduit or passage throughout their length, and suitably the largest cross-dimension of the bore may be up to 10 mm for large torso wounds, and up to 2 mm for limb wounds.

The tube walls should suitably thick enough to withstand any positive or negative pressure on them. However, the prime purpose of such tubes is to convey fluid irrigant and exudate through the length of the apparatus flow path, rather than to act as pressure vessels. The tube walls may suitably be at least 25 micron thick. The bore or any perforations, apertures, holes, openings, orifices, slits or slots along the pipes, etc. or in the hollow body or each of the hollow bodies may be of small cross-dimension. They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the fluid reservoir and/or the rest of the system in which the fluid moves by ultraviolet, gamma or electron beam irradiation.

This way, in particular reduces or eliminates contact of internal surfaces and the fluid with any sterilising agent.

Examples of other methods of sterilisation of the fluid also include e.g. the use of:
- ultrafiltration through microapertures or micropores, e.g. of 0.22 to 0.45 micron maximum cross-dimension, to be selectively impermeable to microbes; and
- fluid antiseptics, such as solutions of chemicals, such as chlorhexidine and povidone iodine; metal ion sources, such as silver salts, e.g. silver nitrate; and hydrogen peroxide although these involve contact of internal surfaces and the fluid with the sterilising agent.

It may be desirable that the interior of the wound dressing, the rest of the system in which the fluid moves, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in increased by continuing addition. Examples of such materials include antibacterial agents (some of which are listed above), and antifungal agents. Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate. may be added to adjust the pH, as may local analgesics/anaesthetics, such as lidocaine/lignocaine hydrochloride, xylocaine (adrenaline, lidocaine) and/or anti-inflammatories, to reduce wound pain or inflammation or pain associated with the dressing. In order to combat the deposition of materials in the flow path from the irrigant, a repellent coating may be used at any point or on any integer in the path in direct contact with the fluid, e.g. on the means for providing aspiration and/or irrigation of the wound or any desired tube or pipe. Examples of coating materials for surfaces over which the aspirating fluid passes include:
- anticoagulants, such as heparin, and
- high surface tension materials, such as PTFE, and polyamides, which are useful for growth factors, enzymes and other proteins and derivatives.

The fluid reservoir for the irrigant may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid. The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system aspiration and irrigation unit, of the dialysate that moves into the aspirating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

Materials deleterious to wound healing that are removed using the apparatus include:
oxidants, such as free radicals, e.g. peroxide and superoxide; iron II and iron III;
all involved in oxidative stress on the wound bed;
proteases, such as serine proteases, e.g. elastase and thrombin; cysteine proteases; matrix metalloproteases, e.g. collagenase; and carboxyl (acid) proteases;
endotoxins, such as lipopolysaccharides;
autoinducer signalling molecules, such as homoserine lactone derivatives, e.g. oxo-alkyl derivatives;
inhibitors of angiogenesis such as thrombospondin-1 (TSP-1), plasminogen activator inhibitor, or angiostatin (plasminogen fragment);
pro-inflammatory cytokines such as tumour necrosis factor alpha (TNFα) and interleukin 1 beta (IL-1β),
oxidants, such as free radicals, e.g., e.g. peroxide and superoxide; and
metal ions, e.g. iron II and iron III, all involved in oxidative stress on the wound bed.

It is believed that aspirating wound fluid aids in removal from of the materials deleterious to wound healing from wound exudate and/or irrigant, whilst distributing materials that are beneficial in promoting wound healing in contact with the wound.

A steady state concentration equilibrium of materials beneficial in promoting wound healing may be set up between in the irrigant and/or wound exudate. Aspirating wound fluid aids in the quicker attainment of this equilibrium. Materials beneficial to wound healing that are distributed include cytokines, enzymes, growth factors, cell matrix components, biological signalling molecules and other physiologically active components of the exudate and/or materials in the irrigant that are potentially or actually beneficial in respect of wound healing, such as nutrients for wound cells to aid proliferation, gases, such as oxygen.

The conduits through which respectively the irrigant and/or wound exudate passes to and from the wound dressing and
i) may have means for modular disconnection and withdrawal of the dressing,
ii) providing an immediate fluid-tight seal or closure over the ends of the conduits and the cooperating tubes in the rest of the apparatus of the invention so exposed,
to prevent continuing passage of irrigant and/or exudate.

The outlet from the means for aspirate flow regulation and/or tubes may be collected and monitored and used to diagnose the status of the wound and/or its exudate.

Any aspirate collection vessel may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the aspirate collection vessel will be largely determined by its function.

To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a further aspect of the present invention there is provided a conformable wound dressing, characterised in that it comprises a backing layer with a wound-facing face which is capable of forming a relatively fluid-tight seal or closure over a wound and has
at least one pipe, which passes through and/or under the wound-facing face to allow irrigation and/or aspiration of the wound, wherein the point at which the or each inlet pipe and the or each outlet pipe passes through and/or under the wound-facing face forming a relatively fluid-tight seal or closure over the wound; and means for stressing the wound bed and optionally tissue surrounding the wound.

The dressing is advantageously provided for use in a bacteria-proof pouch.

Examples of suitable forms of such wound dressings are as described by way of example hereinbefore.

In a third aspect of the present invention there is provided a method of treating wounds to promote wound healing using the apparatus for aspirating, irrigating and/or cleansing wounds of the present invention.

The present invention will now be described by way of example only with reference to the accompanying drawings in which, in all schematics, the means for applying stress to the wound bed omitted for clarity.

FIG. 1 is a schematic view of an apparatus for aspirating, irrigating and/or cleansing a wound according to the present invention that has a single device for moving fluid through the wound applied to the aspirate in the fluid offtake tube downstream of and away from the wound dressing,
in combination with means for supply flow regulation, connected to a fluid supply tube, and means for aspirate flow regulation, connected to a fluid offtake tube.

Figure 2:
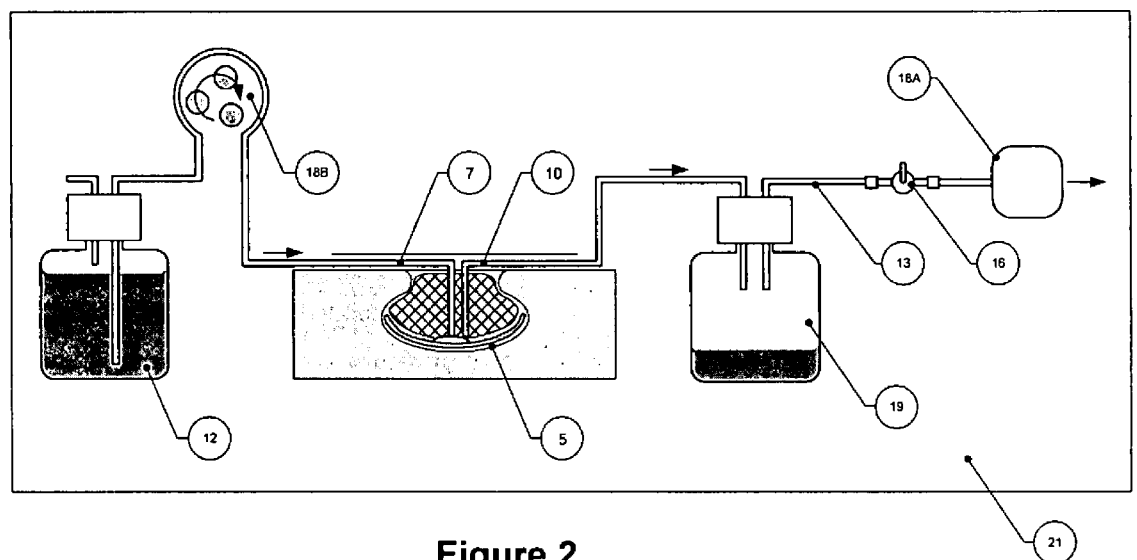

FIG. 2 is a schematic view of another apparatus for aspirating, irrigating and/or cleansing a wound according to the present invention that has a first device for moving fluid through the wound applied to the aspirate in the fluid offtake tube downstream of and away from the wound dressing, with means for aspirate flow regulation, connected to a fluid offtake tube;
and a second device for moving fluid through the wound applied to the irrigant in the fluid supply tube upstream of and towards the wound dressing.

FIGS. 3 to 8 are views of conformable wound dressings for aspirating and/or irrigating wounds.

In these, FIGS. 3a to 5a are plan views of the wound dressings, and FIGS. 3b, 4b, 5b, 6, 7 and 8a are cross-sectional side views of the wound dressings. FIG. 8b shows an isometric view of a stack of layers in an exploded inlet manifold.

FIGS. 9a to d are variants of a two-pump system with essentially identical, and identically numbered, components as in FIG. 2, except that there is a pump bypass loop, a filter downstream of the aspirate collection vessel, and a bleed regulator, such as a rotary valve, connected to the fluid offtake tube or to the wound space, for the regulation of the positive or negative pressure applied to the wound.

Figure 9A:
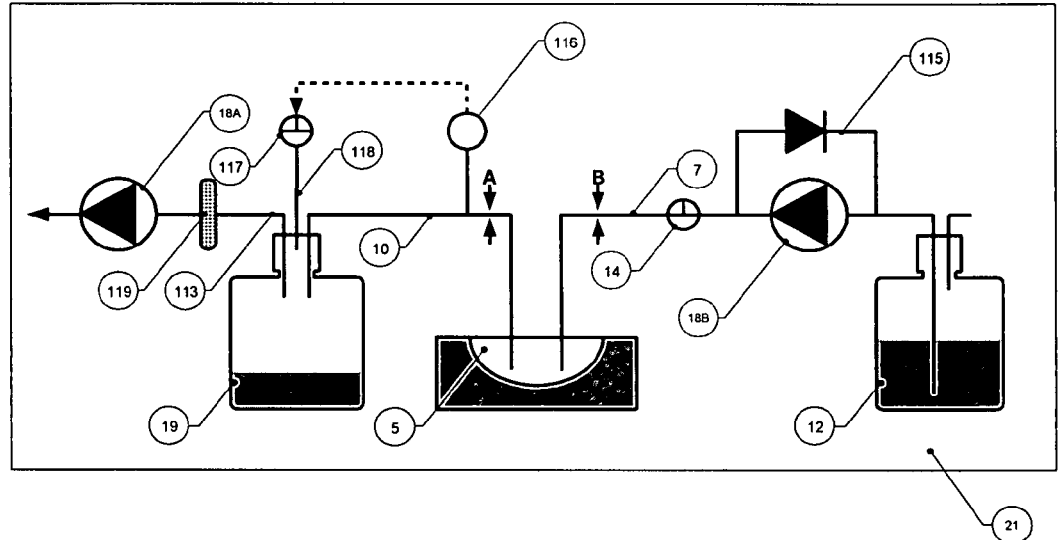
Figure 9B:
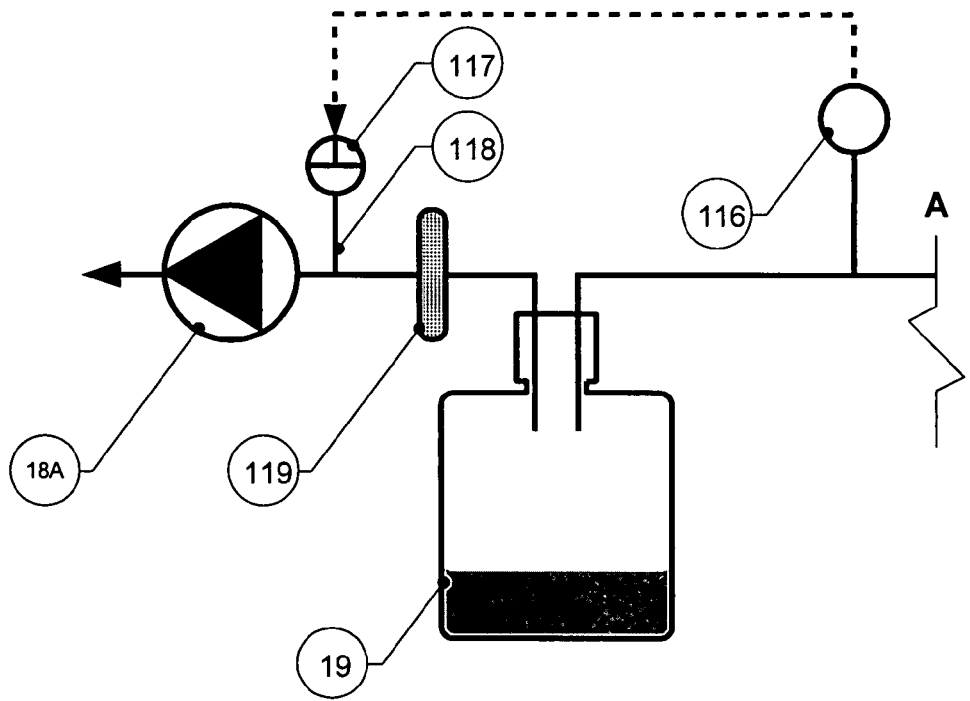
Figure 9C:
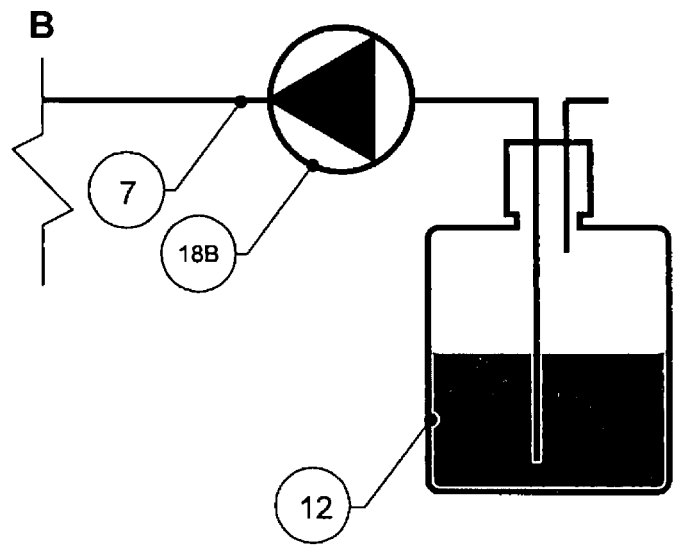
Figure 9D:
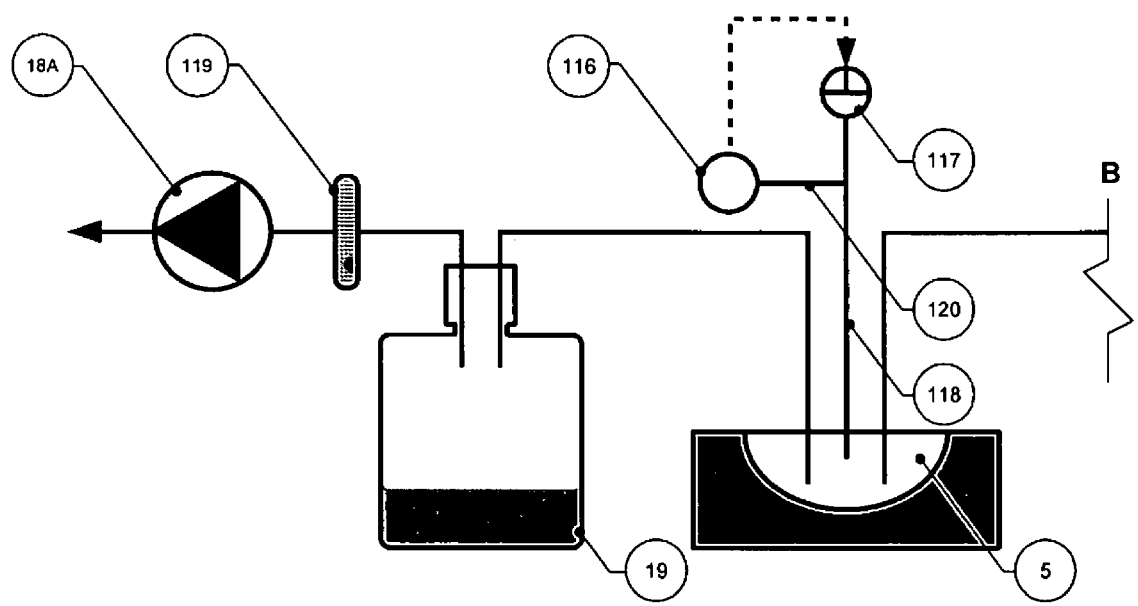
Figure 10A:
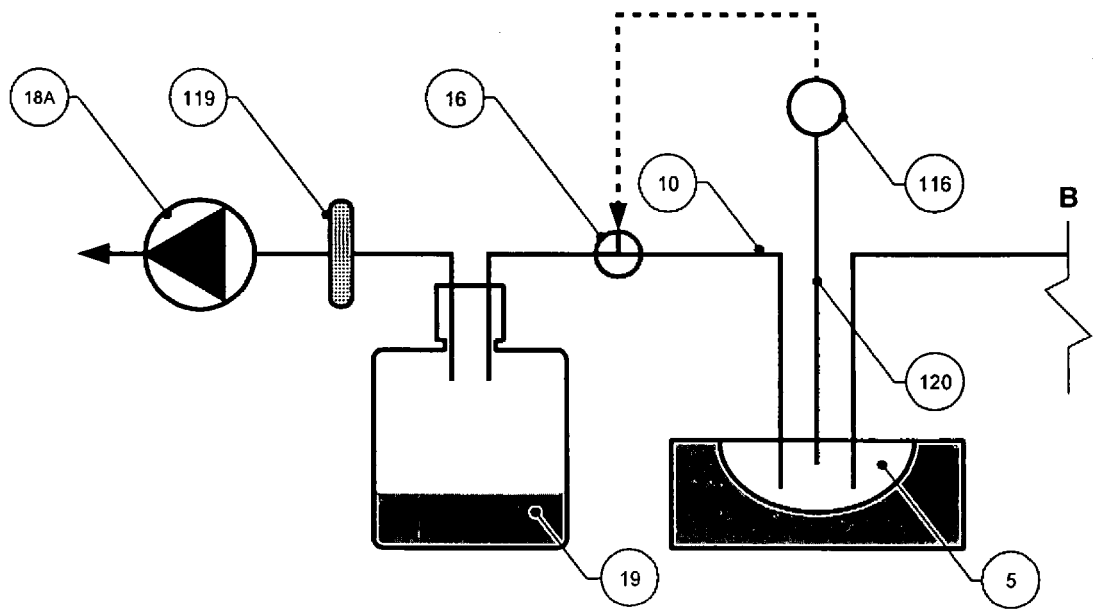
Figure 10B:
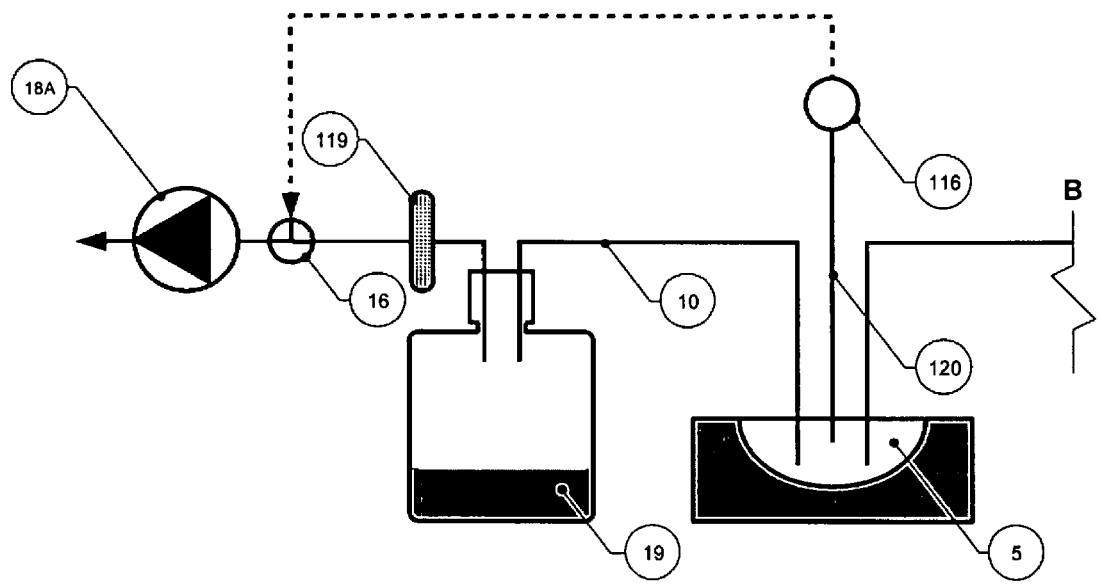
Figure 10C:
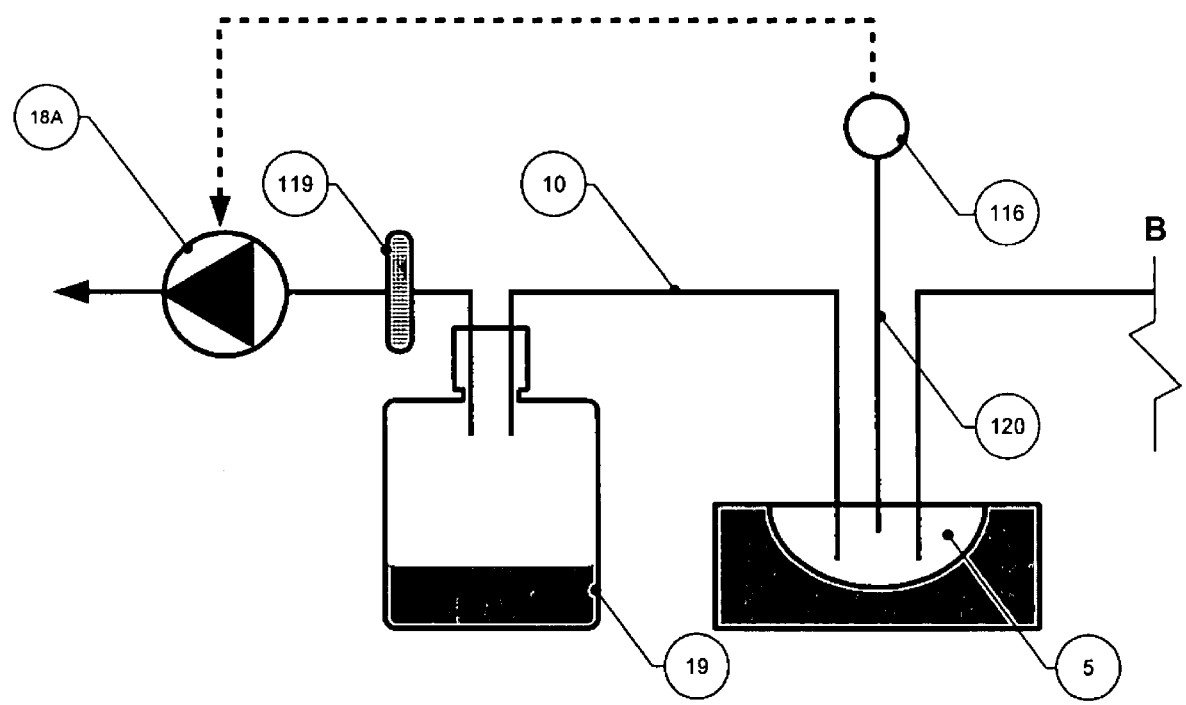

FIGS. 10a to c are variants of a two-pump system with essentially identical, and identically numbered, components as in FIG. 9, except that they have various means for varying the regulation of the positive or negative pressure applied to the wound.

Figure 11A:
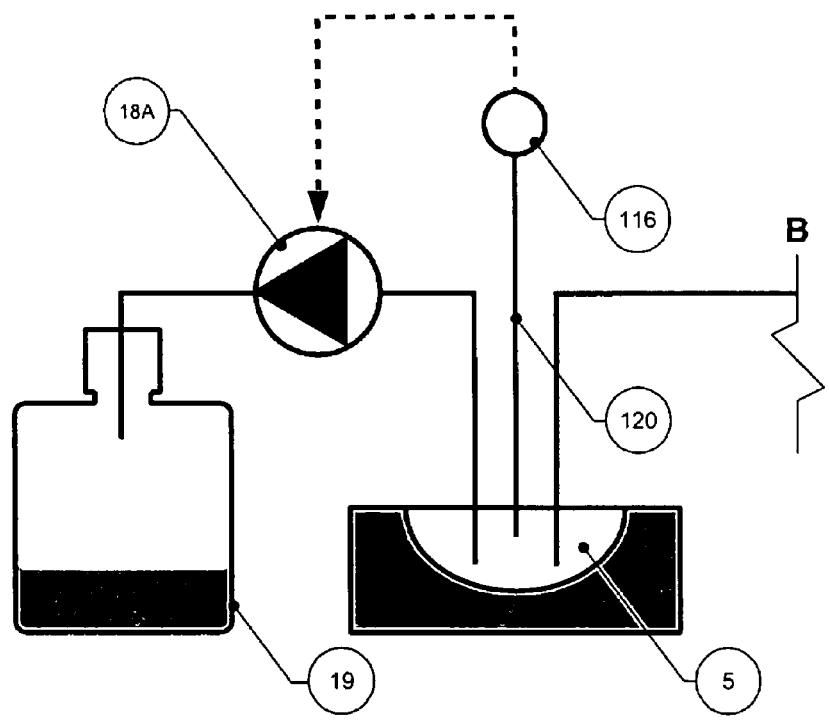

FIGS. 11a and b are variants of a two-pump system with essentially identical, and identically numbered, components as in FIGS. 9a to d. However, they have alternative means for handling the aspirate flow to the aspirate collection vessel under negative or positive pressure to the wound in simultaneous aspiration and irrigation of the wound, including in FIG. 11b a third device for moving fluid into a waste bag.

Figure 12:
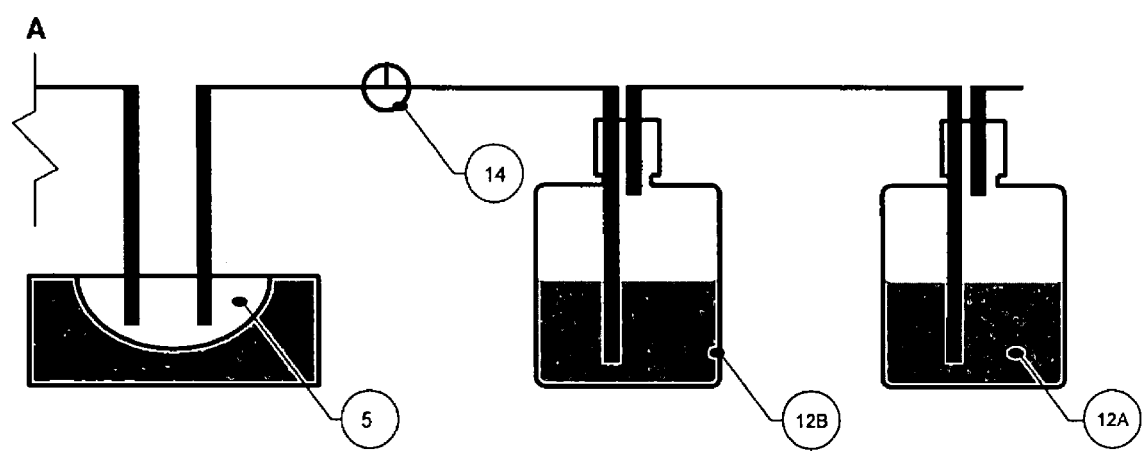

FIG. 12 is a single-pump system essentially with the omission from the apparatus of FIGS. 9a to d of the second device for moving irrigant fluid into the wound dressing.

Referring to FIG. 1, the apparatus (1) for aspirating, irrigating and/or cleansing wounds comprises a conformable wound dressing (2), having
a backing layer (3) which is capable of forming a relatively fluid-tight seal or closure (4) over a wound (5) and
one inlet pipe (6) for connection to a fluid supply tube (7), which passes through the wound-facing face of the backing layer (5) at (8), and
one outlet pipe (9) for connection to a fluid offtake tube (10), which passes through the wound-facing face at (11),
the points (8), (11) at which the inlet pipe and the outlet pipe passes through and/or under the wound-facing face forming a relatively fluid-tight seal or closure over the wound;
the inlet pipe being connected via means for supply flow regulation, here a valve (14), by the fluid supply tube (7) to a fluid reservoir (12), and
the outlet pipe (9) being connected via means for aspirate flow regulation, here a valve (16) and a fluid offtake tube (10) to waste, e.g. to a collection bag (not shown);
a device for moving fluid through the wound (17), here a diaphragm pump (18), e.g. preferably a small portable diaphragm pump, acting on the fluid aspiration tube (13) to apply a low negative pressure on the wound; and
the valve (14) in the fluid supply tube (7), the valve (16) in the fluid offtake tube (10), and the diaphragm pump (18), providing means for providing simultaneous aspiration and irrigation of the wound (17),
such that fluid may be supplied to fill the flowpath from the fluid reservoir via the fluid supply tube (via the means for supply flow regulation) and moved by the device through the flow path.

The Operation of the Apparatus is as Described Hereinbefore.

Referring to FIG. 2, the apparatus (21) is a variant two-pump system with essentially identical, and identically numbered, components as in FIG. 1, except that there is no means for supply flow regulation in the fluid supply tube (7) from the fluid reservoir (12B), and there is a first device for moving fluid through the wound (17), here a diaphragm pump (18A), e.g. preferably a small portable diaphragm pump, acting on the fluid aspiration tube (13) downstream of and away from the wound dressing to apply a low negative pressure on the wound; with means for aspirate flow regulation here a valve (16) connected to the fluid offtake tube (10) and a vacuum vessel (aspirate collection jar) (12A); and a second device for moving fluid through the wound (17), here a peristaltic pump (18B), e.g. preferably a small portable diaphragm pump, applied to the irrigant in the fluid supply tube (7) upstream of and towards the wound dressing, the first device (18A) and second device (18B), and the valve (16) in the fluid offtake tube (10), and the diaphragm pump (18), providing means for providing simultaneous aspiration and irrigation of the wound (17), such that fluid may be supplied to fill the flowpath from the fluid reservoir via the fluid supply tube (via the means for supply flow regulation) and moved by the devices through the flow path.

The Operation of the Apparatus is as Described Hereinbefore

Figure 3A:
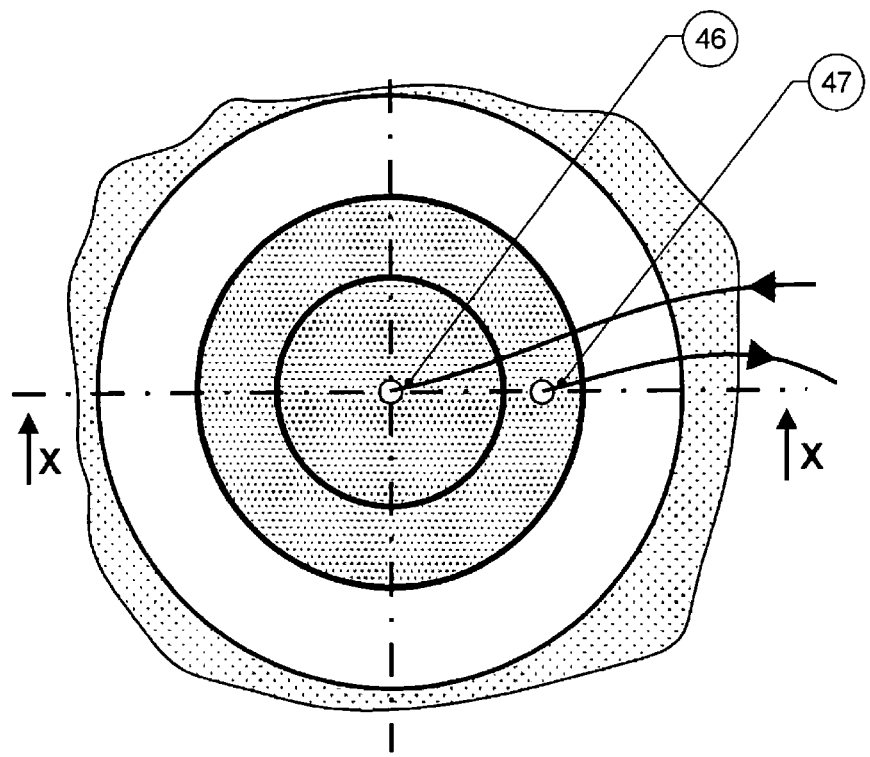
Figure 3B:
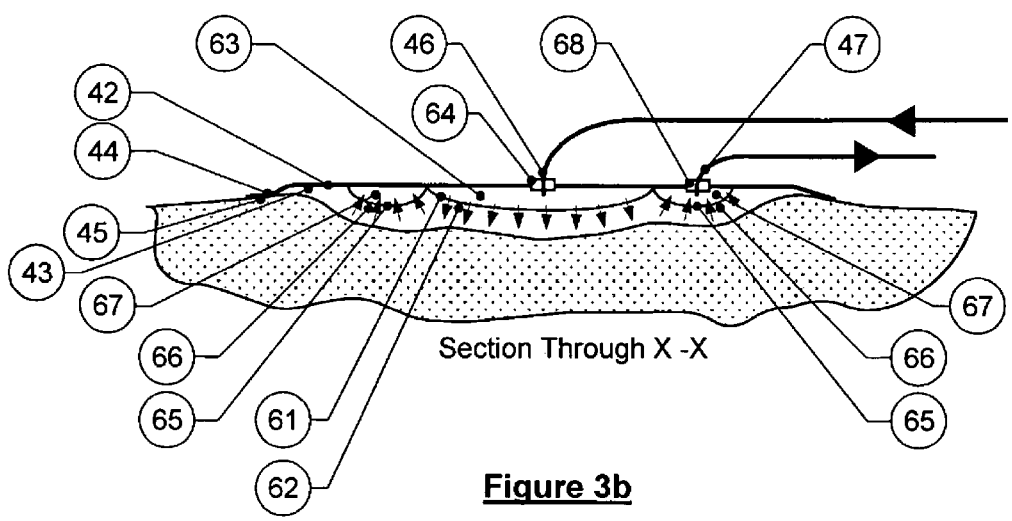

Referring to FIGS. 3a and 3b, a wound dressing suitable for shallower wounds is shown. This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the circulating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Figure 4A:
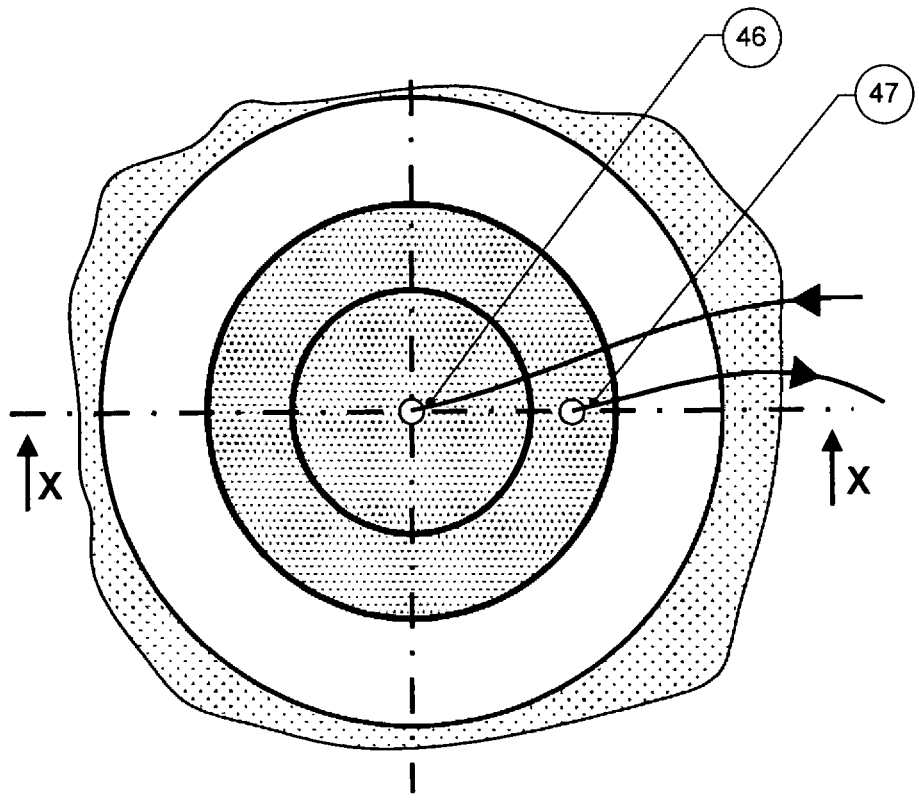
Figure 4B:
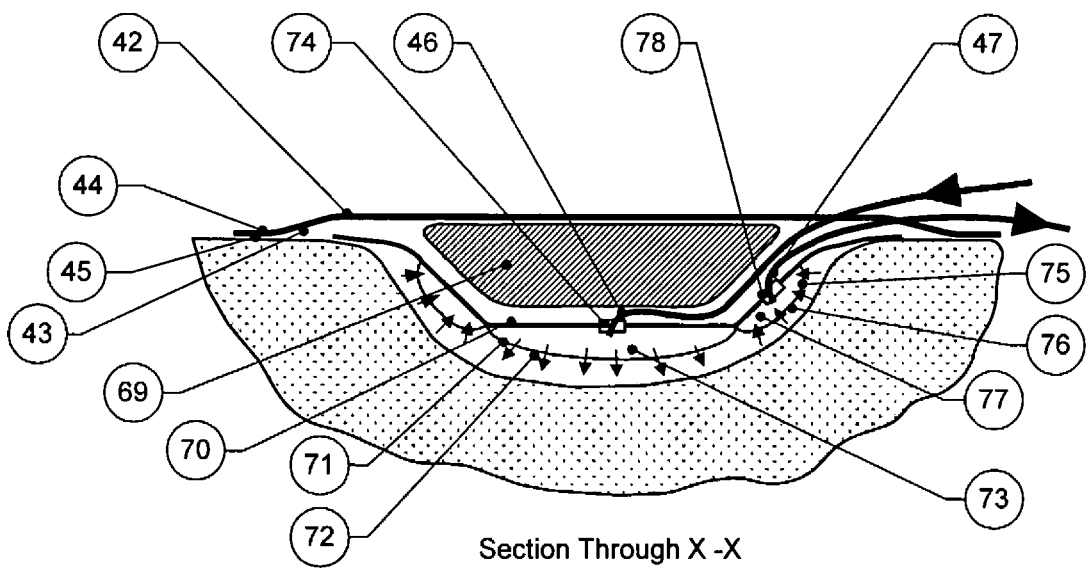

Referring to FIGS. 4a and 4b, a variant of the dressing of FIGS. 3a and 3b that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It is permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the circulating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (77) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42). This is illustrated in FIGS. 4a and 4b.

Figure 5A:
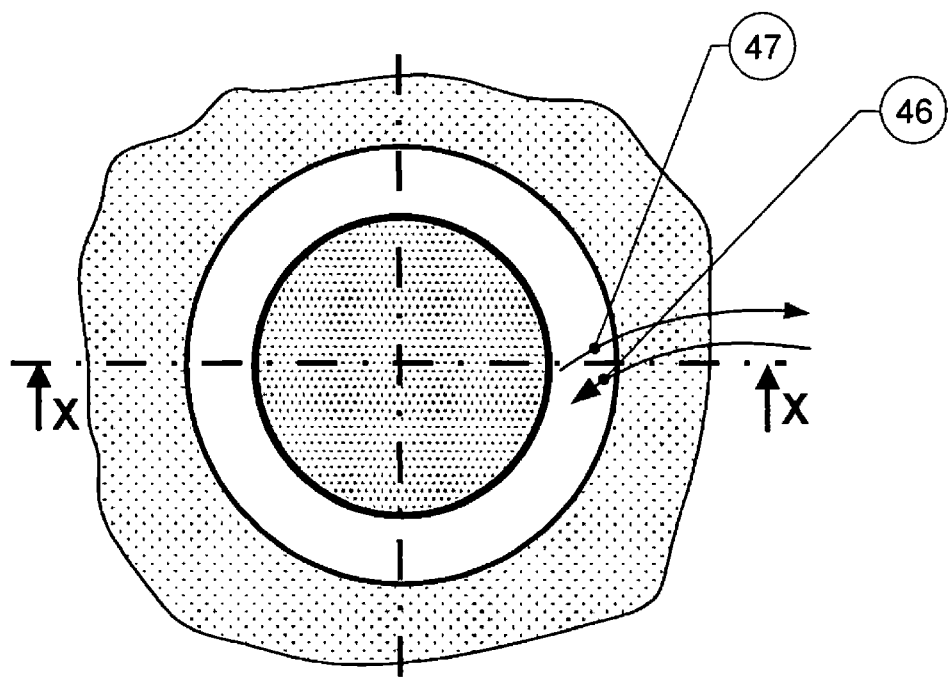
Figure 5B:
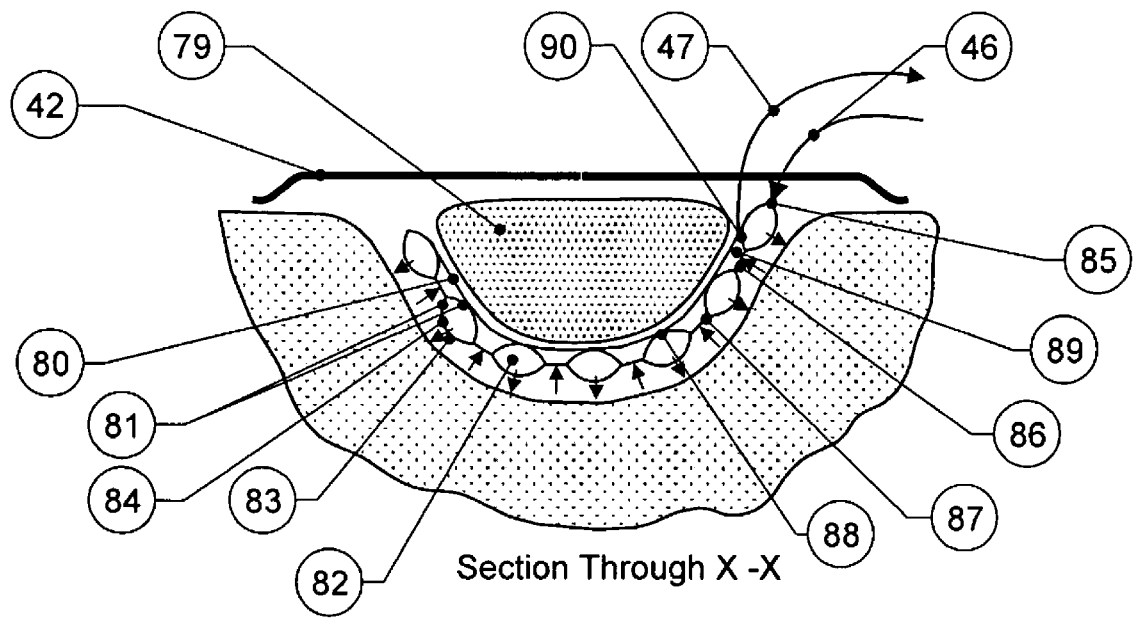

Referring to FIGS. 5a and 5b, a dressing that is a more suitable form for deeper wounds is shown.

This comprises a circular backing layer (42) and a filler (79), in the form of an inverted generally hemispherical integer, e.g. a resilient elastomeric foam or a hollow body filled with a fluid, e.g. a gel that urges it to the wound shape, and permanently unattached to the backing layer.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with perforations (83) along its length on the outer surface (84) of the dish formed by the membrane (81) and an opening (85) at the outer end of its spiral helix, through which the channel (82) communicates with the inlet pipe (46), and thus effectively forms an inlet pipe manifold that delivers the circulating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Figure 6:
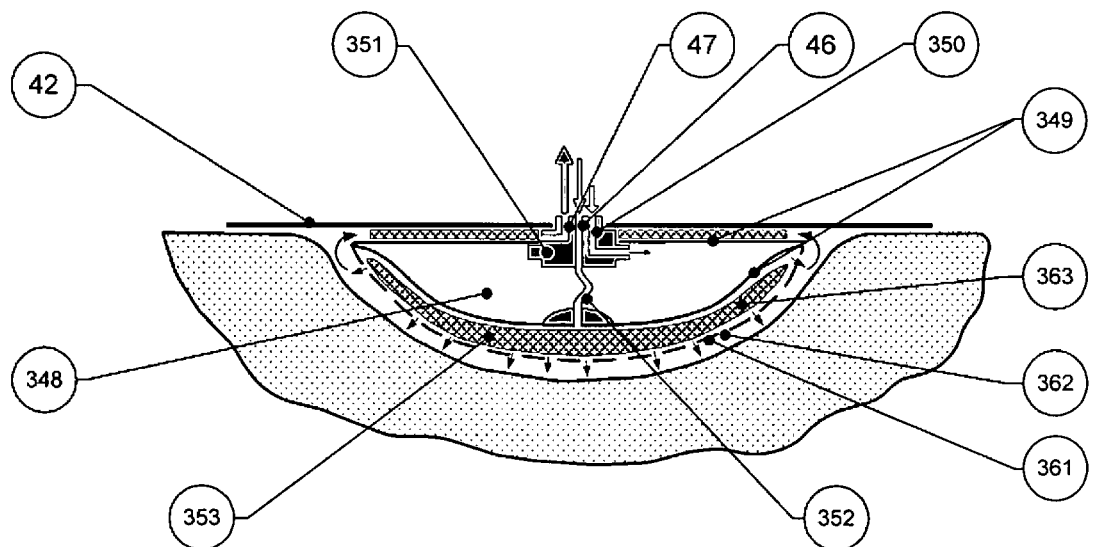
Figure 7:
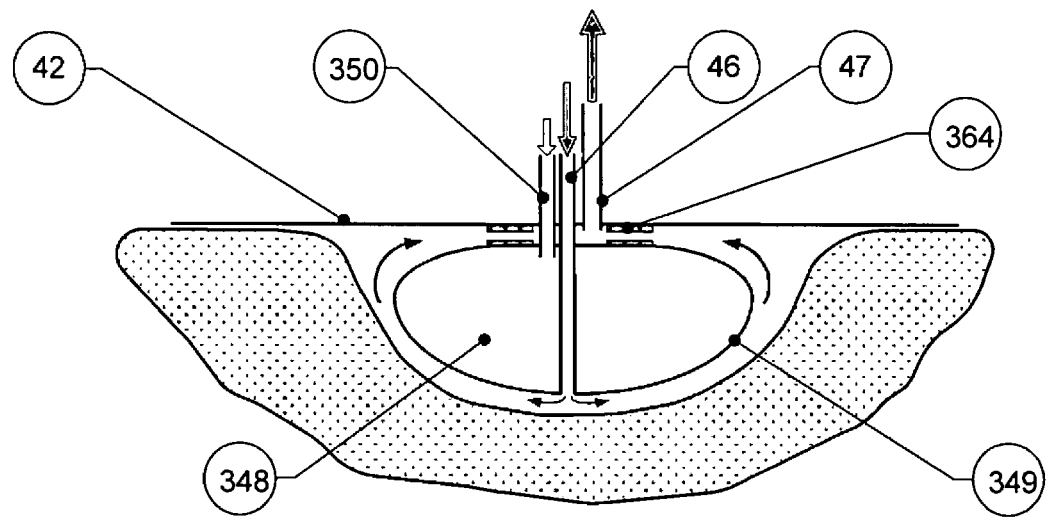
Figure 8A:
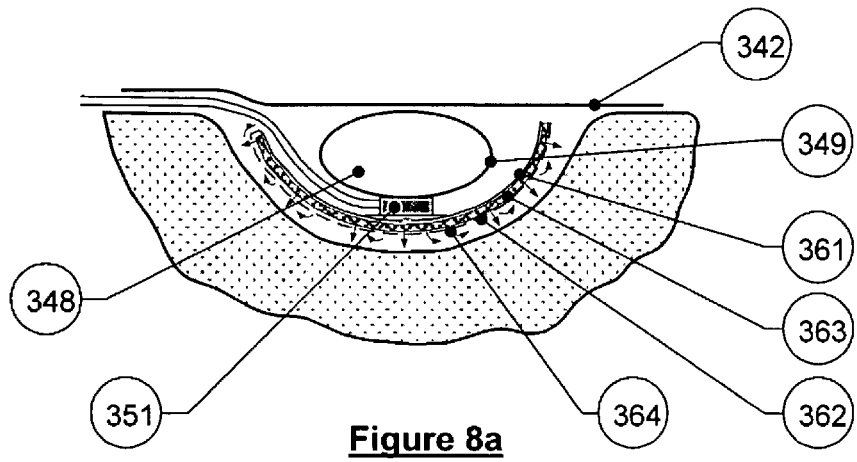
Figure 8B:
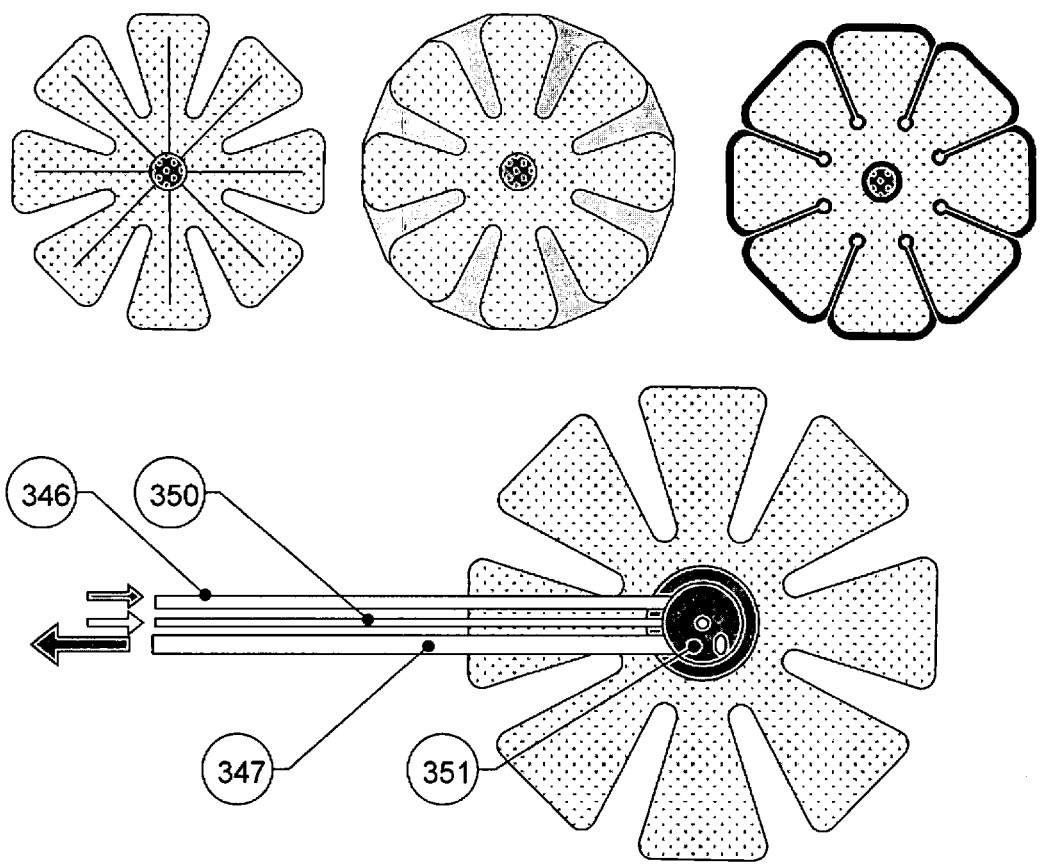

Referring to FIGS. 6 and 7, these forms of the dressing are provided with a wound filler (348) under a circular backing layer (42).

This comprises respectively a generally downwardly domed or oblately spheroidal conformable hollow body, defined by a membrane (349) which is filled with a fluid, here air or nitrogen, that urges it to the wound shape.

An inflation inlet pipe (350), inlet pipe (46) and outlet pipe (47) are mounted centrally in the boss (351) in the backing layer (42) above the hollow body (348). The inflation inlet pipe (350) communicates with the interior of the hollow body (348), to permit inflation of the body (348). Though such inflation of the hollow body (348) the stress applied to the wound can be varied by varying the pressure within the hollow body (348).

The inlet pipe (46) extends in a pipe (352) effectively through the hollow body (348). The outlet pipe (47) extends radially immediately under the backing layer (42).

In FIG. 6, the pipe (352) communicates with an inlet manifold (353), formed by a membrane (361) with apertures (362) that is permanently attached to the filler (348) by heat-sealing.

It is filled with foam (363) formed of a suitable material, e.g. a resilient thermoplastic. Preferred materials include reticulated filtration polyurethane foams with small apertures or pores.

The filler (348) is permanently attached to the backing layer via a boss (351), which is e.g. heat-sealed to the backing layer (42).

In FIG. 7, the outlet pipe (47) communicates with a layer of foam (364) formed of a suitable material, e.g. a resilient thermoplastic. Again, preferred materials include reticulated filtration polyurethane foams with small apertures or pores.

In both of FIGS. 6 and 7, in use, the pipe (352) ends in one or more openings that deliver the irrigant fluid directly from the wound bed over an extended area.

Similarly, the outlet pipe (47) effectively collects the fluid radially from the wound periphery when the dressing is in use.

The form of the dressing shown in FIGS. 6 and 7 is a more suitable layout for deeper wounds.

Referring to FIG. 8 (*a* and *b*), another form for deeper wounds is shown. This comprises a circular, or more usually square or rectangular backing layer (342) and a chamber (363) in the form of a deeply indented disc much like a multiple Maltese cross or a stylised rose.

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 8*b*, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that can be filled with a fluid, here air or nitrogen, that urges it to the wound shape. An inflation inlet pipe (350) is mounted centrally in a first boss (370) in the backing layer (342) above the hollow body (348). The inflation inlet pipe (350) communicates with the interior of the hollow body (348), to permit inflation of the body (348). Again, this inflation of the hollow body (348) is conveniently a means to apply stress to the wound.

A moulded hat-shaped boss (351) is mounted centrally on the upper impervious membrane (361) of the chamber (363). It has three internal channels, conduits or passages through it (not shown), each with entry and exit apertures.

The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing.

They extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Referring to FIG. 9*a*, the apparatus (21) is a variant two-pump system with essentially identical, and identically numbered, components as in FIG. 2.

Thus, there is a means for supply flow regulation, here a valve (14) in the fluid supply tube (7) from the fluid reservoir (12B), and a first device for moving fluid through the wound (17), here a fixed-speed diaphragm pump (18A), e.g. preferably a small portable diaphragm pump, acting not on the fluid aspiration tube (13), but on an air aspiration tube (113) downstream of and away from an aspirate collection vessel (12A) to apply a low negative pressure on the wound through the aspirate collection vessel (12A); with a second device for moving fluid through the wound (17), here a fixed-speed peristaltic pump (18B), e.g. preferably a small portable peristaltic pump, applied to the irrigant in the fluid supply tube (7) upstream of and towards the wound dressing, the first device (18A) and second device (18B), and the valve (14) in the fluid supply tube (7), providing means for providing simultaneous aspiration and irrigation of the wound (17), such that fluid may be supplied to fill the flowpath from the fluid reservoir via the fluid supply tube (via the means for supply flow regulation) and moved by the devices through the flow path.

There is no means for aspirate flow regulation, e.g. a valve connected to the fluid offtake tube (10).

Since first device (18A) and second device (18B) are fixed-speed, the valve (14) in the fluid supply tube (7) provides the sole means for varying the irrigant flow rate and the low negative pressure on the wound.

The Following Extra Features are Present:

The second device, the fixed-speed peristaltic pump (18B), is provided with means for avoiding over-pressure, in the form of a bypass loop with a non-return valve (115). The loop runs from the fluid supply tube (7) downstream of the pump (18B) to a point in the fluid supply tube (7) upstream of the pump (18B).

A pressure monitor (116) connected to the fluid offtake tube (10) has a feedback connection to a bleed regulator, here a motorised rotary valve (117) on a bleed tube (118) running to and centrally penetrating the top of the aspirate collection vessel (12A). This provides means for holding the low negative pressure on the wound at a steady level.

A filter (119) downstream of the aspirate collection vessel (12A) prevents passage of gas- (often air-) borne particulates, including liquids and micro-organisms, from the irrigant and/or exudate that passes into the aspirate collection vessel (12A) into the first device (18A), whilst allowing the carrier gas to pass through the air aspiration tube (113) downstream of it to the first device (18A). The operation of the apparatus is as described hereinbefore Referring to FIG. 9*b*, this shows an alternative layout of the essentially identical, and identically numbered, components in FIG. 9*a* downstream of point A in FIG. 9*a*. The bleed tube (118) runs to the air aspiration tube (113) downstream of the filter (119), rather than into the aspirate collection vessel (12*a*). This provides means for holding the low negative pressure on the wound at a steady level. The operation of the apparatus is as described hereinbefore Referring to FIG. 9*c*, this shows an alternative layout of the essentially identical, and identically numbered, components in FIG. 9*a* upstream of point B in FIG. 9*a*. The second device (18B) is a variable-speed pump, and the valve (14) in the fluid supply tube (7) is omitted. The second device (18B) is the sole means for varying the irrigant flow rate and the low negative pressure on the wound. The operation of the apparatus is as described hereinbefore Referring to FIG. 9d, this shows an alternative layout of the essentially identical, and identically numbered, components in FIG. 9a downstream of point B in FIG. 9a.

The pressure monitor (116) is connected to a monitor offtake tube (120) and has a feedback connection to the bleed regulator, motorised rotary valve (117) on a bleed tube (118) running to the monitor offtake tube (120). This provides means for holding the low negative pressure on the wound at a steady level. The operation of the apparatus is as described hereinbefore Referring to FIG. 10a, this shows another alternative layout of the essentially identical, and identically numbered, components in FIG. 9a downstream of point B in FIG. 9a. The pressure monitor (116) is connected to a monitor offtake tube (120) and has a feedback connection to a means for aspirate flow regulation, here a motorised valve (16) in the air aspiration tube (113) downstream of the filter (119).

This provides means for aspirate flow regulation and for holding the low negative pressure on the wound at a steady level. The operation of the apparatus is as described hereinbefore Referring to FIG. 10b, this shows another alternative layout of the essentially identical, and identically numbered, components in FIG. 10a downstream of point B in FIG. 9a. The pressure monitor (116) is connected to a monitor offtake tube (120) and has a feedback connection to a means for aspirate flow regulation, here a motorised valve (16), in the fluid offtake tube (10) upstream of the aspirate collection vessel (12a).

This provides means for aspirate flow regulation and for holding the low negative pressure on the wound at a steady level. The operation of the apparatus is as described hereinbefore Referring to FIG. 10c, this shows another alternative layout of the essentially identical, and identically numbered, components in FIG. 10a downstream of point B in FIG. 9a. The pressure monitor (116) is connected to a monitor offtake tube (120) and has a feedback connection to a variable-speed first device (18A), here a variable-speed pump, downstream of the filter (119), and the valve (16) in the fluid offtake tube (10) is omitted.

This provides means for aspirate flow regulation and for holding the low negative pressure on the wound at a steady level. The operation of the apparatus is as described hereinbefore.

Referring to FIG. 11a, this shows another alternative layout of the essentially identical, and identically numbered, components in FIG. 10c downstream of point B in FIG. 9a, and alternative means for handling the aspirate flow to the aspirate collection vessel under negative or positive pressure to the wound.

The pressure monitor (116) is connected to a monitor offtake tube (120) and has a feedback connection to a variable-speed first device (18A), here a variable-speed pump, upstream of the aspirate collection vessel (12A), and the filter (119) and the air aspiration tube (113) are omitted. This provides means for aspirate flow regulation and for holding the low negative pressure on the wound at a steady level. The operation of the apparatus is as described hereinbefore.

Figure 11B:
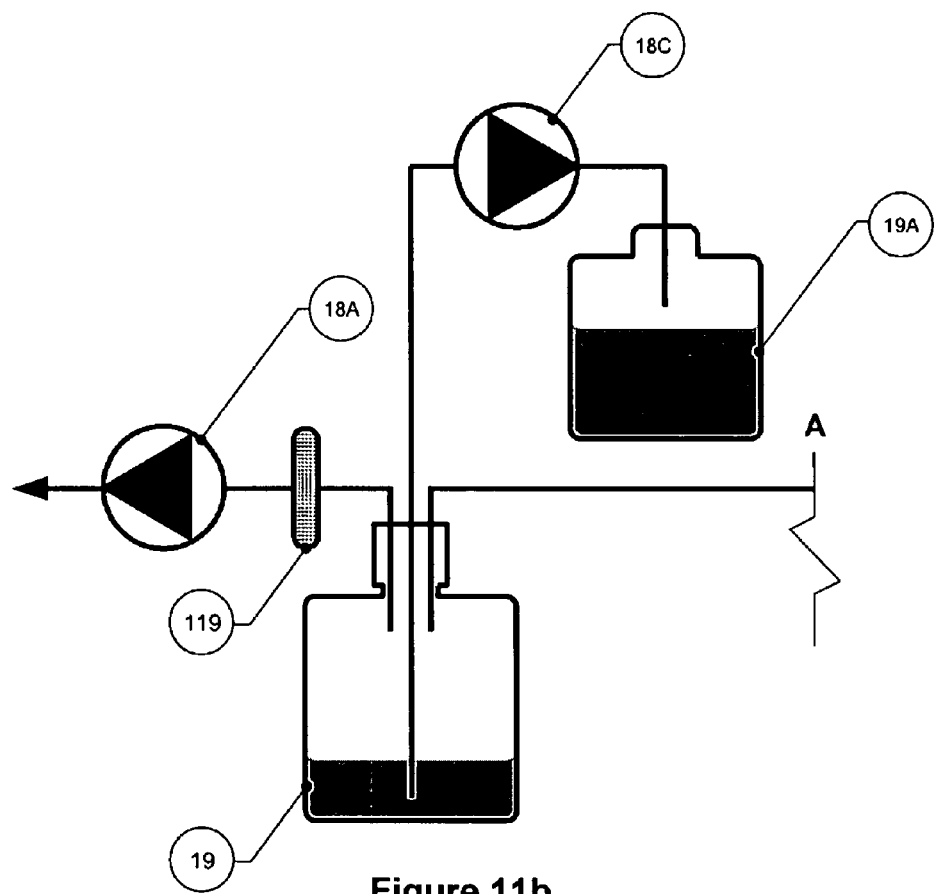

Referring to FIG. 11b, this shows another alternative layout of the essentially identical, and identically numbered, components in FIG. 10c downstream of point B in FIG. 9a, and alternative means for handling the aspirate flow to the aspirate collection vessel under negative or positive pressure to the wound. The pressure monitor (116) is omitted, as is the feedback connection to a variable-speed first device (18A), here a variable-speed pump, downstream of the aspirate collection vessel (12A) and the filter (119). A third device (18C), here a fixed-speed pump, provides means for moving fluid from the aspirate collection vessel (12A) into a waste bag (12C). The operation of the apparatus is as described hereinbefore.

Referring to FIG. 12, this shows an alternative layout of the essentially identical, and identically numbered, components in FIG. 9a upstream of point A in FIG. 9a.

It is a single-pump system essentially with the omission from the apparatus of FIG. 9a of the second device for moving irrigant fluid into the wound dressing. The operation of the apparatus is as described hereinbefore.

Demonstration of In Vitro Effects of Applying Stress to Cells in a Simulated Wound.

Objective

To determine the total amount of collagen deposited by human dermal fibroblasts on silica Flexercell plates following macrostress treatment over a period of time.

Methods

Cells

Human dermal fibroblasts (HS8/BS04) were used. Experiments were performed whereby fibroblasts ($5 \times 10^5$ per well) were seeded in silicone membrane 6 well plates (Flexercell), supplied by Flexcell Intl. Hillsborough, N.C. and subjected to a range of 'macrostress' (macrostress as used in this example refers to stress applied to the cells by way of mechanical stretching) treatments for 48 hours, whereby the cells were subjected to a strewn of 15% (i.e. 15% elongation of the cell substrate) at a frequency of 0.1 Hz on a cycle having a sine wave profile. The Flexercell, Tension Plus™ system is a computer-driven instrument that simulates biological strain conditions using vacuum pressure to deform cells cultured on flexible, matrix-bonded growth surfaces of BioFlex® series culture plates. Following experimentation, media was removed, the cells were washed in PBS and stored at −70° C. until analysed for collagen levels.

The cells were exposed to sequential (SEQ) or simultaneous (SIA) irrigation/aspiration. For SIA, a flow rate of 0.1 ml per minute was used. For sequential, 10 empty/fill cycles were performed over the 48 hour period, each empty/fill taking 1 hour to complete. The media used was DMEM/10% FCS.

Collagen Quantification

The collagen content present on the 6 well plates was determined using a hydroxyl proline quantification assay which 2 ml papain buffer was used to digest any collagen due to the larger surface area.

RT-PCR

Relative quantification of plasminogen inhibitor activiator 2 (PIA-2) and collagen 1a gene expression was determined using the Taqman RT-PCR machine.

RNA Extraction

Cells were scraped from the well in RLN buffer and the RNA from 3 sample wells were pooled using one RNeasy mini column. Control RNA was extracted from fibroblasts grown to confluence in a T175 flask.

RNA extraction from fibroblasts was performed using reagents and protocols described in RNeasy Mini Handbook (Qiagen) and RLN buffer (50 mM Tris-HCl, Sigma, lot 033K8418; 140 mM NaCl, Sigma, lot 013K8930; 1.5 mM $MgCl_2$, Sigma, lot 082K8938; 0.5% (v/v) Igepal (Sigma, lot 102K0025); 10 µl/ml β-mercaptoethanol, Sigma, lot 102K0025, made up to volume in Molecular Biology grade water (Sigma, lot, 23K2444).

Following elution from the spin column in 50 µl water, the RNA was quantified using a spectrophotometer.

cDNA Preparation cDNA was prepared from RNA using Omniscript reverse transcription kit (Qiagen) with Random Hexamer primers (Applied Biosystems, lot G07487). The reaction was completed by heating for 1 hour at 37° C. and stored at −20° C. until required.

RT-PCR Primers

Three gene products were selected as they had previously been shown to be up-regulated during Flexercell Macrostress treatment (Kessler, et al, JBC, 276, 39, 36575-36585, 2001). Primers were synthesised by MWG Biotech.

```
Collagen 1a:
F-5' ACA TGC CGA GAC TTG AGA CTC A
R-5' GCA TCC ATA GTA CAT CCT TGG TTA GG
```

(from Wong et al, Tissue Engineering, 8, 6, 979-2002)

```
PAI-2:
F-5' AAT GCA TCC ACA GGG GAT TA
R-5' CGC AGA CTT CTC ACC AAA CA
```

(Designed using Primer 3 software, sequence from accession no. H81869)

```
18S rRNA
F-5' CGG CTA CCA CAT CCA AGG AA
R-5' GCT GGA ATT ACC GCG GCT
```

(18S rRNA housekeeping gene primers previously designed and synthesised by Sigma).

SYBR Green

SYBR green reagent (Applied Biosystems, lot 0505023) master mix was prepared as per manufacturers protocol. Briefly, 50% v/v SYBR green, 0.05% primer 1, 0.05% primer 2, made up to 100% in RNase free water. 5 µl cDNA template and 45111 SYBR green added per well.

PCR

The RT-PCR was performed using 7700 Taqman RT-PCR system (SOP/BC/227). The run conditions were:
1) 50° C. for 2 minutes
2) 95° C. for 10 minutes
3) 95° C. for 15 seconds
4) 60° C. for 1 minute Conditions 3 and 4 repeated for a total of 40 cycles.

To ensure a single PCR product had been amplified, a melt analysis on the product was performed using the following conditions:
1) 95° C. for 15 seconds
2) 60° C. for 20 seconds
3) 95° C. for 15 seconds A ramp time of 19.59 minutes between stage 2 and 3 was used to determine the degradation temperature.

Results and Discussion

Collagen Quantification

The amount of collagen present in each well of a six well Flexercell plate was determined using the hydroxyproline quantification assay. Fibroblast cells, seeded at either $5 \times 10^3$ or $5 \times 10^5$ per well were grown on laminin coated plates for 72 hours. The absorbance values determined following analysis were very low, showing that the amount of collagen present was also very low. Unfortunately, an error was made when preparing the hydroxyproline standard curve whereby the stock solution was not diluted 10 fold so it was not possible to give an amount of hydroxyproline present. This error would only have affected the standards. The low values showed that this assay was not suitable for measuring such low collagen contents.

A second hydroxyproline determination assay was performed using gas chromatography (GS-MS). This analysis also revealed very low collagen content present in the 6 well plates.

RT-PCR

As the cells only had 72 hours to proliferate and synthesis new collagen, a short length of time, it was decided to look for changes in the level of gene expression, which, generally relates to changes in the amount of protein synthesised as the cells proliferate.

The genes of interest chosen to investigate were collagen 1a and plasminogen activator inhibitor 2 (PIA-2) genes as these had previously been shown to be induced in stressed collagen lattices (Kessler et al, JBC, 276, 39, pp. 36575-36585, 2001). The level of gene expression of the genes of interest is expressed as a ratio against 18S rRNA, a housekeeping gene, shown previously (Kessler et al, 2001) to remain at a steady level of expression.

For the RT-PCR experiments, fibroblasts were grown and subjected to 15% strain, 0.1 Hz frequency for 48 hours, with control samples not being subjected to these conditions. Also, they were subjected to either continuous irrigate aspiration of media (SIA), or a series of 1 hour empty/fill cycles (SEQ). All systems were kept under vacuum of ~25 mbar below atmospheric.

The level of PAI-2 gene expression was determined in fibroblasts subjected to the four sets of conditions described above. The results are shown in table 1.

TABLE 1

| | |
|---|---|
| SIA only | 1.6 |
| SEQ only | 5.3 |
| SIA plus macrostress | 5.4 |
| SEQ plus macrostress | 5.3 |

The results show that there is an increase in the level of PAI-2 gene expression when fibroblasts in the SIA system are subjected to macrostress (at 15% strain, 0.1 Hz frequency; n=1). However, the level of expression is also elevated in both SEQ and SEQ plus macrostress fibroblasts. Unfortunately, due to technical difficulties during the initial macrostress Flexercell experiments, only one set of experimental plates were available for analysis.

Conclusions

RT-PCR analysis of PAI-2 gene expression showed an increase in the level of expression in SIA plus macrostress compared to SIA only. This demonstrates the effect of macrostress on the activity of the cells in the in vitro wound simulation, and supports the role of macrostress in wound healing.

There was no difference in the level of expression in SEQ and SEQ plus macrostress fibroblasts.

Due to technical difficulties, these results are from an n=1, therefore care needs to be taken when interpreting the results. However, the results indicate that application of macrostress to cells during SIA irrigation leads to increase levels of cell activity, and possibly of collagen production. This reflects on increase in healing activity where stress is applied.

The results of the SEQ analysis are puzzling, and may be the results of an unidentified error in the protocol. Future experiments will be required to confirm this. An alternative hypothesis is that additional stresses induced by the fill/empty cycle may have inadvertently resulted in stress being applied to the control population.

The invention claimed is:

1. An apparatus for aspirating, irrigating and/or cleansing a wound, comprising:
  a fluid flow path, comprising:
    a conformable wound dressing, having a backing layer which is capable of forming a relatively fluid-tight seal or closure over a wound, thereby creating a space between the wound and the backing layer,
    an inlet pipe in fluid communication with the space between the wound and the backing layer to allow irrigation of the wound; and
    an outlet pipe in communication with the space between the wound and the backing layer to allow aspiration of the wound;
  a fluid reservoir that, in use, provides an irrigation fluid directly or indirectly to the inlet pipe;
  a first device for directly or indirectly moving fluid through the inlet pipe or the outlet pipe;
  a first regulator for directly or indirectly regulating fluid moving through the inlet pipe or the outlet pipe; and
  a second device for moving fluid through the other of the inlet pipe or the outlet pipe as compared to the first device and/or a second regulator for regulating fluid moving through the other of the inlet pipe or the outlet pipe as compared to the first regulator;
  means for applying stress to the wound bed and/or tissue surrounding the wound comprising at least one expandable and contractible fluid-inflatable body capable of applying pressure to the wound bed;
  wherein:
    the fluid-inflatable body comprises an inflation inlet, is partially filled with an elastically resilient material, such as an elastomeric foam, and defines a sealed space in communication with the inflation inlet.

2. The apparatus of claim 1 comprising both a second device for moving fluid through the outlet pipe and a second regulator for regulating fluid moving through the outlet pipe and wherein, in use, the first device directly or indirectly moves fluid through the inlet pipe and the first regulator directly or indirectly regulates fluid moving through the inlet pipe.

3. The apparatus of claim 1 comprising a second device for moving fluid through the outlet pipe, wherein, in use, the first device directly or indirectly moves fluid through the inlet pipe while the second device moves fluid through the outlet pipe so as to provide simultaneous aspiration and irrigation of the wound.

4. The apparatus of claim 1 in which the means for applying stress to the wound bed is capable of applying an optionally varying positive and/or negative pressure to the wound bed.

5. The apparatus of claim 1 wherein the fluid-inflatable body is inflatable by a gas, liquid, gas in liquid aerosol and/or a gel.

6. The apparatus of claim 1 wherein the manifold covers and contacts a significant area of the wound bed with openings that deliver the fluid directly to the wound bed over an extended area.

7. The apparatus of claim 1 wherein the manifold comprises of one or more inflatable hollow bodies defined by a film sheet or membrane.

8. The apparatus of claim 1 wherein the manifold covers 50% or greater of the wound bed.

9. The apparatus of claim 1 wherein the fluid-inflatable body comprises a substantially flat film, sheet or membrane, defining a chamber, pouch or other structure of the backing layer.

10. The apparatus of claim 1 comprising an inflation and/or deflation pump for inflating or deflating the fluid-inflatable body.

11. The apparatus of claim 10 wherein the inflation and/or deflation pump is reversible.

12. The apparatus of claim 10 wherein the inflation and/or deflation pump is a piston pump or rotary pump.

13. The apparatus of claim 12 wherein the inflation and/or deflation pump is a peristaltic pump.

14. The apparatus of claim 1 in which the means for applying stress to the wound bed is capable of varying the pressure by up to 50% above and below atmospheric pressure.

15. The apparatus of claim 1 in which the means for applying stress to the wound bed is capable of varying pressure in regular or irregular cycles.

16. The apparatus of claim 15 in which the frequency of regular or irregular cycles is between 1 and 48 per 24 hour period.

17. The apparatus of claim 1 in which the means for applying stress to the wound bed is capable of varying pressure in regular or irregular pulses.

18. The apparatus of claim 17 in which frequencies of regular pulses for the stimulation of the healing of wounds is from 1 to 3000 per minute (0.016- 50 Hz).

19. The apparatus of claim 18 in which maximum amplitude for the pulses is up to 10 mm Hg above and below the baseline pressure.

20. The apparatus of claim 1 in which the means for applying stress to the wound is capable of varying pressure in regular or irregular cycles and regular or irregular pulses, the pulses being superimposed on the cycles.

21. The apparatus of claim 1 wherein the means for applying stress to the wound bed includes a magnetic fluid in a chamber or other hollow structure.

22. The apparatus of claim 1 wherein the means for applying stress to the wound bed comprises means to bleed fluid into the flow path of the apparatus.

23. The apparatus of claim 3 wherein the first and/or second device for moving fluid through the wound is a variable-throughput device.

24. The apparatus of claim 23 wherein the first and/or second device is a variable-speed pump.

25. The apparatus of claim 24 wherein the first and/or second device for moving fluid through is a reciprocating pump or a rotary pump.

26. The apparatus of claim 25 wherein the first device is a diaphragm pump.

27. The apparatus of claim 25 wherein the second device is a peristaltic pump.

28. The apparatus of claim 3 wherein the variable-throughput device is capable of pulsed, continuous, variable and/or automated and/or programmable fluid movement.

29. The apparatus of claim 1 wherein the apparatus is capable of applying a negative pressure within the wound dressing of up to 50% atm.

30. The apparatus of claim 29 comprising at least one body in the flow path to, over and from the wound bed which has sufficient resilience against the pressure to allow any significant compression or decompression of the fluid occur.

31. The apparatus of claim 1 wherein the one or more pipes comprise a manifold which covers and contacts a significant area of the wound bed with openings for delivering and/or receive fluid directly to/from the wound bed over an extended area.

32. The apparatus of claim 1 wherein securing means are provided to secure the wound dressing to the site of the wound.

33. An apparatus for aspirating, irrigating and/or cleansing a wound comprising:
   a wound dressing comprising:
      a backing layer with a wound-facing face which is capable of forming a relatively fluid-tight seal or closure over a wound;
      an inlet pipe in fluid communication with a space between the wound and the backing layer to allow irrigation of the wound; and
      an outlet pipe in communication with the space between the wound and the backing layer to allow aspiration of the wound;
   means for applying stress to the wound bed and optionally tissue surrounding the wound comprising at least one expandable and contractible fluid-inflatable body, the fluid inflatable body configured to provide a positive and/or negative pressure to the wound and/or tissue surrounding the wound;
   a first device for moving fluid through the wound dressing to the wound and/or moving fluid from the wound; and
   a second device for moving fluid through the wound dressing to the wound and/or moving fluid from the wound; and
   means for aspirate flow regulation connected to the outlet pipe and/or means for supply flow regulation connected to the inlet pipe;
   wherein:
      the fluid-inflatable body comprises an inflation inlet, is partially filled with an elastically resilient material, such as an elastomeric foam, and defines a sealed space in communication with the inflation inlet.

34. The apparatus of claim 33, wherein the wound dressing is provided in a bacteria-proof pouch.

35. A method of operation of an apparatus for aspirating, irrigating and/or cleansing a wound, said method comprising:
   applying the apparatus of claim 1 to the wound;
   conforming the backing layer of the wound dressing to the shape of the bodily part in which the wound is to form a relatively fluid tight seal or closure;
   activating the first device to move irrigant to the wound; and
   activating the means for applying stress to the wound bed and optionally tissue surrounding the wound.

36. The method of claim 35 wherein activating means for applying stress to the wound bed and optionally tissue surrounding the wound comprises activating means to apply optionally varying positive and/or negative pressure to the wound bed.

37. The method of claim 35 wherein activating the first device to move irrigant to the wound comprises activating the first device to move an irrigant fluid through the at least one inlet and to move an aspirant fluid out of the at least one outlet pipe.

38. The method of claim 35 wherein the flow rate of fluid to the dressing is in the range of 1 to 1500 ml/hour.

39. The method of claim 35 wherein the flow rate of total fluid out of the dressing is in the range of 1 to 2000 ml/hour.

40. The method of claim 35 wherein activating the first device to move irrigant to the wound comprises activating simultaneous irrigation and aspiration of the wound.

41. The method of claim 35 wherein activating the first device to move irrigant to the wound comprises activating sequential irrigation and aspiration of the wound.

42. The method of claim 35 wherein the apparatus is run at a negative pressure of up to 50% atm.

43. The method of claim 35 comprising applying the stress intermittently.

44. The apparatus of claim 1 wherein the at least one expandable and contractible body is cyclically inflated and deflated by admitting and releasing a fluid from the module during use.

45. The method of claim 35 comprising stressing the wound by applying a cyclical positive and negative pressure to the wound in accordance with a systolic-diastolic asymmetric sawtooth waveform.

46. The method of treating a wound of claim 45 wherein the systolic-diastolic asymmetric sawtooth waveform has a frequency of about 60 to 100 per minute.

47. The method of claim 35 comprising applying a varying pressure to the wound in accordance with a sinusoidal waveform.

48. The method of claim 35 comprising varying a pressure within the wound cover between a positive and a negative value, wherein the positive value is above atmospheric pressure and the negative value is below atmospheric pressure.

49. The method of claim 35 comprising varying the pressure to the wound between at least two negative pressure values, wherein each negative pressure value is below atmospheric pressure.

* * * * *

UNITED STATES PATENT AND TRADEMARK OFFICE
CERTIFICATE OF CORRECTION

PATENT NO.      : 8,235,955 B2
APPLICATION NO. : 11/919355
DATED           : August 7, 2012
INVENTOR(S)     : Blott et al.

It is certified that error appears in the above-identified patent and that said Letters Patent is hereby corrected as shown below:

On the Title page, Item [56]

In column 1 (page 3) at line 18, Under Other Publications, change "salmoncida:" to --salmonicida:--.

In the Specification

In column 3 at line 18, Change "and or" to --and/or--.

In column 3 at line 23-24, Change "revascularisation," to --revascularization,--.

In column 7 at line 67, Change "bed" to --bed.--.

In column 11 at line 32-33, Change "equilibrium" to --equilibrium.--.

In column 13 at line 5, Change "minute" to --minute.--.

In column 13 at line 8, Change "pumps Flexible" to --pumps, Flexible--.

In column 19 at line 4, Change "tube:" to --tube;--.

In column 21 at line 42, Change "wound," to --wound.--.

In column 22 at line 32, Change "the may" to --they may--.

In column 24 at line 51, Change "a" to --as--.

In column 25 at line 15, Change "flange" to --flange.--.

In column 26 at line 49, Change "boustrophedic" to --boustrophedonic--.

In column 27 at line 45, Change "phosphate." to --phosphate--.

In column 31 at line 30-31, Change "Hereinbefore" to --Hereinbefore.--.

In column 31 at line 53, Change "frustroconical," to --frustoconical,--.

In column 34 at line 54, Change "hereinbefore" to --hereinbefore.--.

In column 34 at line 62, Change "hereinbefore" to --hereinbefore.--.

In column 35 at line 3, Change "hereinbefore" to --hereinbefore.--.

In column 35 at line 13, Change "hereinbefore" to --hereinbefore.--.

Signed and Sealed this
Thirteenth Day of August, 2013

Teresa Stanek Rea
*Acting Director of the United States Patent and Trademark Office*

In column 35 at line 23-24, Change "hereinbefore" to --hereinbefore.--.

In column 35 at line 35-36, Change "hereinbefore" to --hereinbefore.--.

In column 36 at line 52, Change "activiator" to --activator--.

In column 38 at line 63, Change "on" to --an--.

In the Claims

In column 42 at line 6, In Claim 37, after "wherein" insert --the wound dressing comprises an inlet and an outlet pipe and--.

In column 42 at line 26, In Claim 44, change "body" to --module--.